(12) United States Patent
Geyer et al.

(10) Patent No.: US 9,393,250 B2
(45) Date of Patent: Jul. 19, 2016

(54) PHTHALOCYANINE COMPOUNDS USEFUL AS RECA INHIBITORS AND METHODS OF USING SAME

(71) Applicant: University of Saskatchewan, Saskatoon (CA)

(72) Inventors: Clarence Ronald Geyer, Saskatoon (CA); Yu Luo, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 0 days.

(21) Appl. No.: 14/394,456

(22) PCT Filed: Apr. 11, 2013

(86) PCT No.: PCT/IB2013/052899
§ 371 (c)(1),
(2) Date: Oct. 14, 2014

(87) PCT Pub. No.: WO2013/153532
PCT Pub. Date: Oct. 17, 2013

(65) Prior Publication Data
US 2015/0087612 A1    Mar. 26, 2015

Related U.S. Application Data

(60) Provisional application No. 61/623,493, filed on Apr. 12, 2012.

(51) Int. Cl.
| | |
|---|---|
| *A61K 31/164* | (2006.01) |
| *A61K 31/357* | (2006.01) |
| *A61K 31/409* | (2006.01) |
| *A61K 31/43* | (2006.01) |
| *A61K 31/496* | (2006.01) |
| *A61K 31/555* | (2006.01) |
| *A61K 31/65* | (2006.01) |
| *A61K 31/7036* | (2006.01) |

(52) U.S. Cl.
CPC ............. *A61K 31/555* (2013.01); *A61K 31/164* (2013.01); *A61K 31/357* (2013.01); *A61K 31/409* (2013.01); *A61K 31/43* (2013.01); *A61K 31/496* (2013.01); *A61K 31/65* (2013.01); *A61K 31/7036* (2013.01)

(58) Field of Classification Search
None
See application file for complete search history.

(56) References Cited

U.S. PATENT DOCUMENTS

| | | | |
|---|---|---|---|
| 6,037,125 A | 3/2000 | Hasty | |
| 6,057,104 A | 5/2000 | Hasty | |
| 6,066,628 A | 5/2000 | Stojiljkovic | |

(Continued)

FOREIGN PATENT DOCUMENTS

| | | |
|---|---|---|
| CA | 2272991 A1 | 5/1998 |
| CA | 2362109 A1 | 8/2000 |

(Continued)

OTHER PUBLICATIONS

Luigi, PLoS ONE, Mar. 2008, vol. 3, Issue 3, e1888.*

(Continued)

*Primary Examiner* — Layla Berry
(74) *Attorney, Agent, or Firm* — Oyen Wiggs Green & Mutala LLP

(57) ABSTRACT

Compounds having the general structural formula (I) wherein X can be any element or compound that can form a coordination complex with phthalocyanine and wherein R1; R2, R3 and R4 are independently anionic moieties, or (II) wherein R1; R2, R3 and R4 are independently anionic moieties, are useful in the potentiation of antibiotic activity, and/or in inhibiting or delaying the development of resistance to antibiotics. R1; R2, R3 and R4 may be —S03-. The compounds may be administered to a subject in conjunction with an antibiotic. The antibiotic may be an activator of the SOS response, and may be a DNA gyrase inhibitor or a topoisomerase inhibitor. Compositions and dosage forms comprising the compounds are provided.

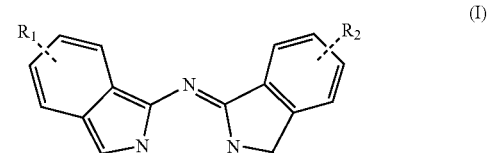

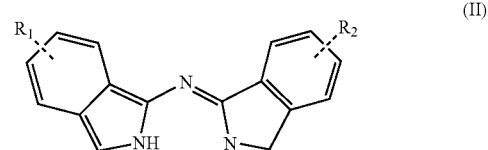

20 Claims, 10 Drawing Sheets

(56) References Cited

U.S. PATENT DOCUMENTS

| | | |
|---|---|---|
| 6,576,759 B2 | 6/2003 | Zeng |
| 6,906,096 B2 | 6/2005 | Alper |
| 7,455,840 B2 | 11/2008 | Romesberg |
| 7,592,154 B2 | 9/2009 | Miller |
| 8,101,357 B2 | 1/2012 | Yaku |
| 2002/0022215 A1 | 2/2002 | Sobsey |
| 2002/0086840 A1 | 7/2002 | Zarling |
| 2002/0137698 A1 | 9/2002 | Ohnishi |
| 2002/0147161 A1 | 10/2002 | Zeng |
| 2003/0229004 A1 | 12/2003 | Zarling |
| 2004/0110944 A1 | 6/2004 | Alper |
| 2006/0111302 A1 | 5/2006 | Romesberg |
| 2006/0199768 A1 | 9/2006 | Singleton |
| 2006/0286574 A1 | 12/2006 | Romesberg |
| 2007/0031874 A1 | 2/2007 | Miller |
| 2007/0287677 A1 | 12/2007 | Kaneda |
| 2008/0153877 A1 | 6/2008 | Adimoolam |
| 2009/0264342 A1 | 10/2009 | Cottarel |
| 2009/0292357 A1 | 11/2009 | McCoy |
| 2010/0029597 A1 | 2/2010 | Cottarel |
| 2010/0184681 A1 | 7/2010 | Eckert |
| 2010/0184683 A1 | 7/2010 | Eckert |
| 2010/0184684 A1 | 7/2010 | Eckert |

FOREIGN PATENT DOCUMENTS

| | | |
|---|---|---|
| CA | 2379608 A1 | 2/2001 |
| CA | 2384733 A1 | 3/2001 |
| CA | 2544018 A1 | 6/2005 |
| CA | 2603179 A1 | 10/2006 |
| CA | 2641895 A1 | 8/2007 |
| CA | 2642264 A1 | 8/2007 |
| CA | 2642754 A1 | 8/2007 |
| CA | 2674084 C | 7/2008 |
| WO | 98/20030 A2 | 5/1998 |
| WO | 00/47231 A2 | 8/2000 |
| WO | 00/53630 A2 | 9/2000 |
| WO | 01/11369 A1 | 2/2001 |
| WO | 01/19397 A1 | 3/2001 |
| WO | 02/02153 A1 | 1/2002 |
| WO | 02/058738 A2 | 8/2002 |
| WO | 03/013488 A2 | 2/2003 |
| WO | 03/061579 A2 | 7/2003 |
| WO | 2004/014294 A2 | 2/2004 |
| WO | 2004/020457 A2 | 3/2004 |
| WO | 2005/056754 A2 | 6/2005 |
| WO | 2005/095613 A1 | 10/2005 |
| WO | 2006/096757 A2 | 9/2006 |
| WO | 2006/108075 A2 | 10/2006 |
| WO | 2007/088392 A1 | 8/2007 |
| WO | 2007/095187 A2 | 8/2007 |
| WO | 2007/097940 A2 | 8/2007 |
| WO | 2008/019292 A2 | 2/2008 |
| WO | 2008/082856 A1 | 7/2008 |
| WO | 2008/094507 A2 | 8/2008 |
| WO | 2009/018219 A2 | 2/2009 |
| WO | 2009/042270 A2 | 4/2009 |
| WO | 2009/154828 A2 | 12/2009 |
| WO | 2010/080819 A1 | 7/2010 |
| WO | 2010/080836 A2 | 7/2010 |

OTHER PUBLICATIONS

Barnard, F.M., et al., "Interaction between DNA gyrase and quinolones: effects of alanine mutations at GyrA subunit residues Ser(83) and Asp(87)", Antimicrob Agents Chemother, 2001, 45(7):1994-2000.

Beaber, J.W., et al., "SOS response promotes horizontal dissemination of antibiotic resistance genes", Nature, 2004, 427(6969):72-74.

Bi, E, et al. "Cell division inhibitors SulA and MinCD prevent formation of the FtsZ ring", J Bacteriol, 1993, 175(4):1118-1125.

Caughey, W.S., et al., "Cyclic tetrapyrrole sulfonation, metals, and oligomerization in antiprion activity", Antimicrob Agents Chemother, 2007, 51(11):3887-3894.

Cirz, R.T., et al., "Inhibition of mutation and combating the evolution of antibiotic resistance", PLoS Biol, 2005, 3(6):1024-1032.

Cirz, R.T., et al., "Side effects may include evolution", Nat Med, 2006, 12(8):890-891.

Cirz, R.T., et al., "Controlling mutation: intervening in evolution as a therapeutic strategy", Crit Rev Biochem Mol Biol, 2007, 42(5):341-354.

Drlica K, et al., "DNA gyrase, topoisomerase IV, and the 4-quinolones", Microbiol Mol Biol Rev, 1997, 61(3):377-392.

Dumoulin, F., et al. "Synthetic pathways to water-soluble phthalocyanines and close analogs", Coor Chem Rev, 2010, 254(23-24):2792-2847.

Farr, S.B., and Kogoma, T., "Oxidative stress responses in *Escherichia coli* and *Salmonella typhimurium*", Microbiol Rev, 1991, 55(4):561-585.

Gotoh, H., et al., "SOS involvement in stress-inducible biofilm formation", Biofouling, 2010, 26(5):603-611.

Hastings, P.J., et al., "Antibiotic-induced lateral transfer of antibiotic resistance", Trends Microbiol, 2004, 12(9):401-404.

Huisman, O., et al., "Cell-division control in *Escherichia coli*: specific induction of the SOS function SfiA protein is sufficient to block septation", Proc Natl Acad Sci USA, 1984, 81(14):4490-4494.

Itaya, K., and Ui, M., "A new micromethod for the colorimetric determination of inorganic phosphate", Clin Chim Acta, 1966, 14:361-366.

Janion, C., "Some aspects of the SOS response system—a critical survey", Acta Biochim Pol, 2001, 48(3):599-610.

Karlin, S. and L. Brocchieri, "Evolutionary conservation of RecA genes in relation to protein structure and function", J Bacteriol, 1996, 178(7):1881-1894.

Kohanski, M., et al., "A common mechanism of cellular death induced by bactericidal antibiotics", Cell, 2007, 130:797-810.

Kohanski, M., et al., "How antibiotics kill bacteria: from targets to networks", Nature Rev Microb, 2010, 8:423-435.

Lee, Andrew M., et al., "A complementary pair of rapid molecular screening assays for RecA activities", Analytical Biochemistry, 2007, 367:247-258.

Li, Y., et al., "Crystal structure of an archaeal Rad51 homologue in complex with a metatungstate inhibitor", Biochemistry, 2009, 48(29):6805-6810.

Lusetti, S.L. and M.M. Cox, "The bacterial RecA protein and the recombinational DNA repair of stalled replication forks", Annu Rev Biochem, 2002, 71:71-100.

Kowalczykowski, S.C., et al., "Biochemistry of homologous recombination in *Escherichia coli*", Microbiol Rev, 1994, 58(3):401-465.

McCool, J.D., et al., Measurement of SOS expression individual *Escherichia coli* K-12 cells using fluorescence microscopy, Mol Microbiol, 2004, 53(5)1343-1357.

McKenzie, G., et al., "The SOS response regulates adaptive mutation", Proc Natl Acad Sci USA, 2000, 97(12):6646-6651.

Oram, M. and L.M. Fisher, "4-quinolone resistance mutations in the DNA gyrase *Escherichia coli* clinical isolates identified by using the polymerase chain reaction", Antimicrobial Agents and Chemotherapy, 1991, 35(2):387-389.

Pereira, J.B., et al., "Phthalocyanine thiopyridinium derivatives as antibacterial photosensitizers", Photochemistry and Photobiology, 2012, 88:537-547.

Peterson, E.J., et al., "High-throughput screening for RecA inhibitors using a transcreener adenosine 5'-O-Diphosphate assay", Assay Drug Dev Technol, 2012, 10(3):260-268.

Priola, S.A., et al., "Prophylactic and therapeutic effects of phthalocyanine tetrasulfonate in scrapie-infected mice", Infect Dis, 2003, 188(5):699-705.

Raymond-Denise, A. and N. Guillen, "Identification of dinR, a DNA damage-inducible regulator gene of Bacillus subtilis", J Bacteriol, 1991, 173(22):7084-7091.

Riesenfeld, C., et al., "Adaptive mutations produce resistance to ciprofloxacin", Antimicrob Agents Chemother, 1997, 41(9):2059-2060.

Rosenberg, S.M., "Evolving responsibly: Adaptive mutation", Nat Rev Genetics, 2001, 2:504-515.

(56) References Cited

OTHER PUBLICATIONS

Sassanfar, M. and J.W. Roberts, "Nature of the SOS-inducing signal in *Escherichia coli*. The involvement of DNA replication", J Mol Biol, 1990, 212(1):79-96.

Sexton, J.Z., et al., "Novel inhibitors of *E. coli* RecA ATPase activity", Curr Chem Genomics, 2010, 4:34-42.

Smith, P.A. and F.E. Romesberg, "Combating bacteria and drug resistance by inhibiting mechanisms of persistence and adaptation", Nat Chem Biol, 2007, 3(9):549-556.

Vila, J., et al., "Detection of mutations in parC in quinolone resistant clinical isolates of *Escherichia coli*", Antimicrob Agents Chemother, 1996, 40(2):491-493.

Wigle, Tim J. and Scott F. Singleton, "Directed molecular screening for RecA ATPase inhibitors", Bioorganic & Medicinal Chemistry Letters, 2007, 17:3249-3253.

Wigle, Tim J., et al., "Inhibitors of RecA activity discovered by high-throughput screening: cell-permeable small molecules attenuate the SOS response in *Escherichia coli*", Journal of Biomedical Screening, 2009, 14(9): 1092-1101.

Yaku, H., et al., "Anionic phthalocyanines targeting G-quadruplexes and inhibiting telomerase activity in the presence of excessive DNA duplexes", Chem Comm, 2010, 46:5740-5742.

Yu, X., et al., "Direct visualization of dynamics and co-operative conformational changes within RecA filaments that appear to be associated with the hydrolysis of adenosine 5'-O-(3-thiotriphosphate)", J Mol Biol, 1992, 225(1):193-216.

Zuluaga, A.F., et al., "Neutropenia induced in outbred mice by a simplified low-dose cyclophosphamide regimen: characterization and applicability to diverse experimental models of infectious diseases", BMC Infect Dis, 2006, 6:55, pp. 1 to 10.

\* cited by examiner

Figure 1 con't
(c)
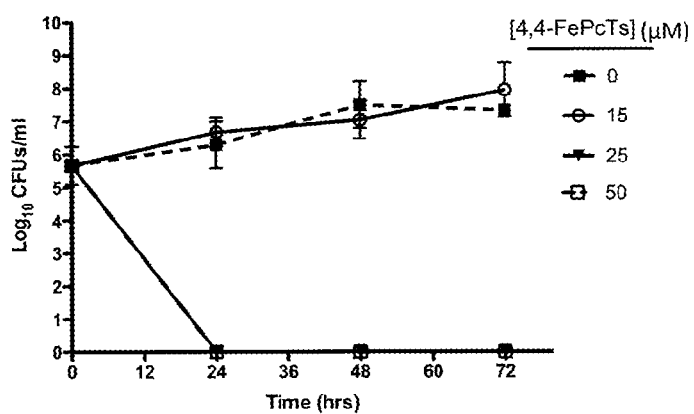
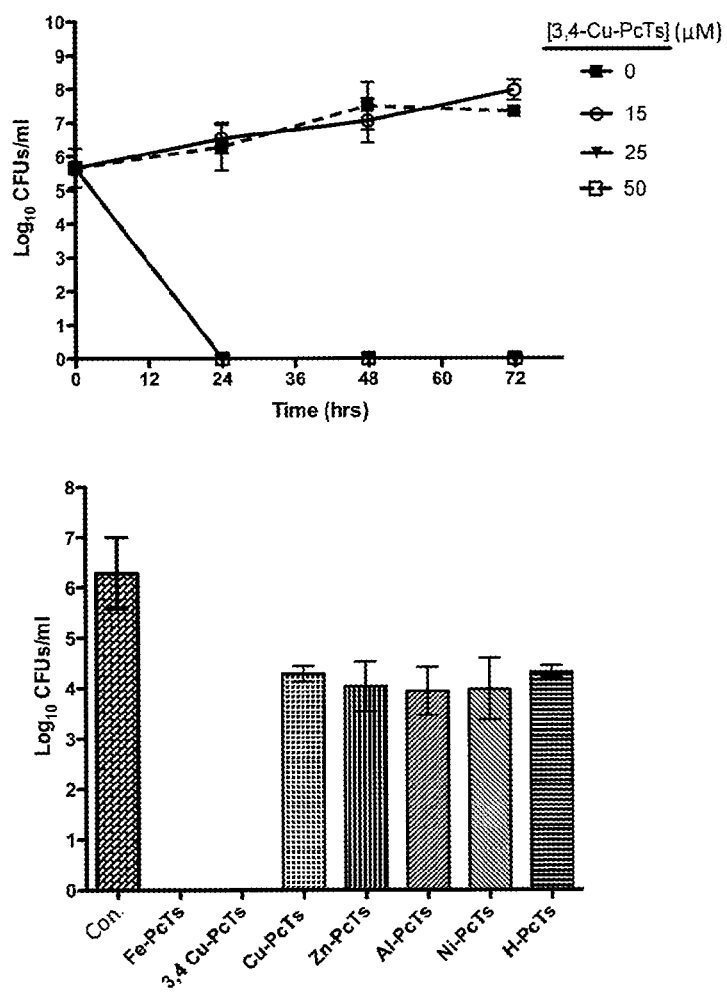
(d)

(a)

(i)

(ii)

(iii)

Figure 2 con't
(b)
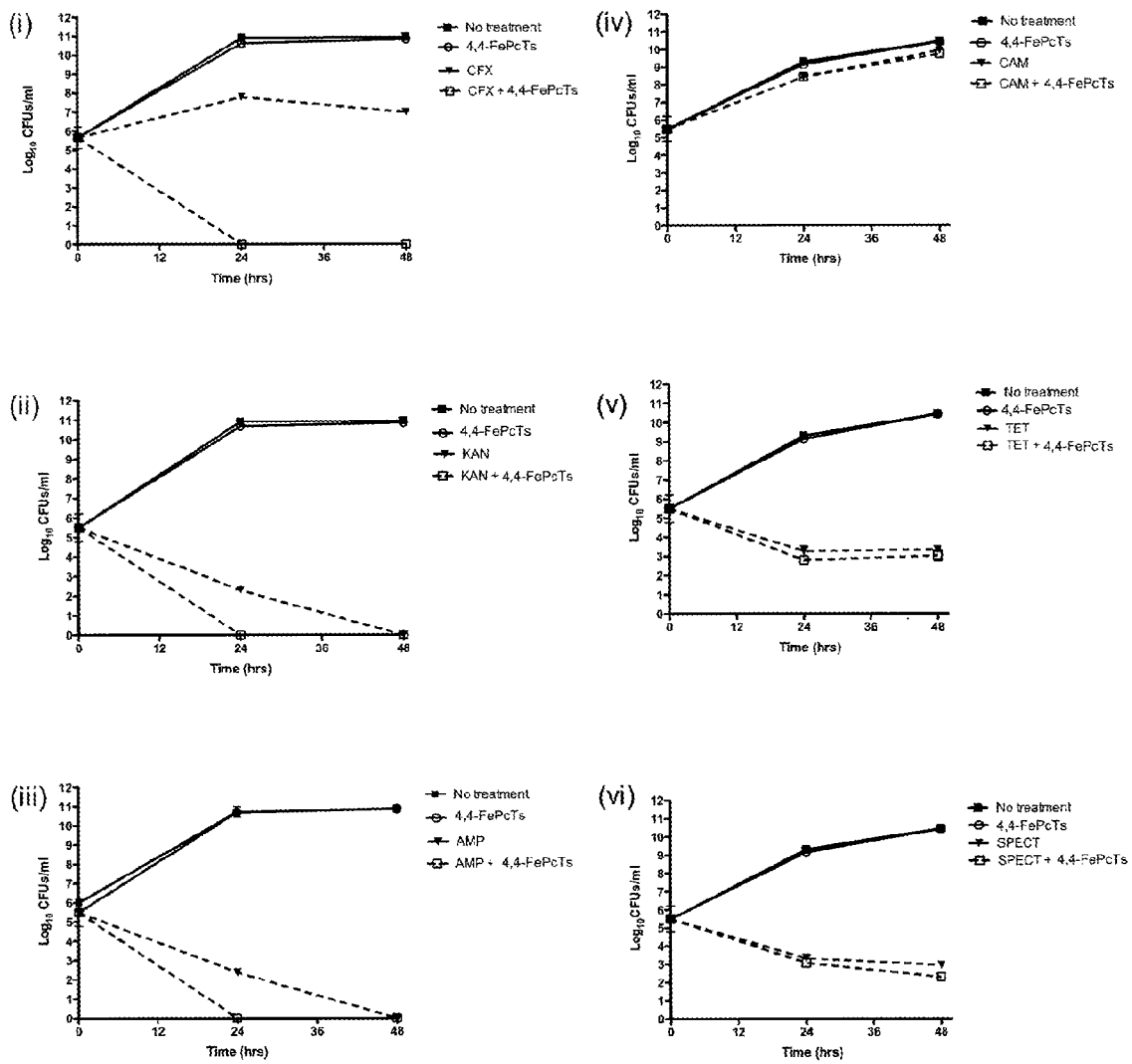

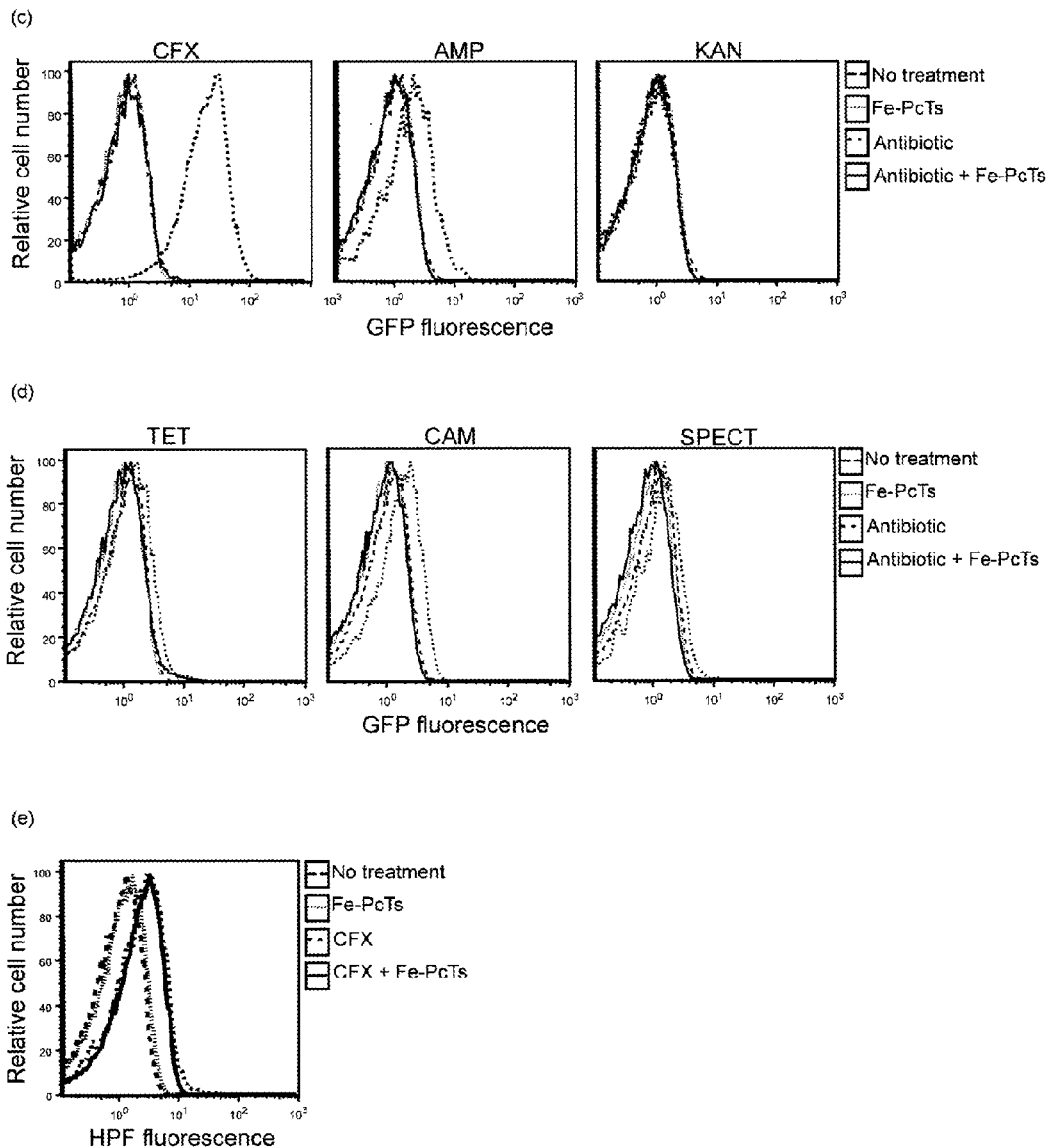
Figure 2 con't

Figure 2 con't
(f)
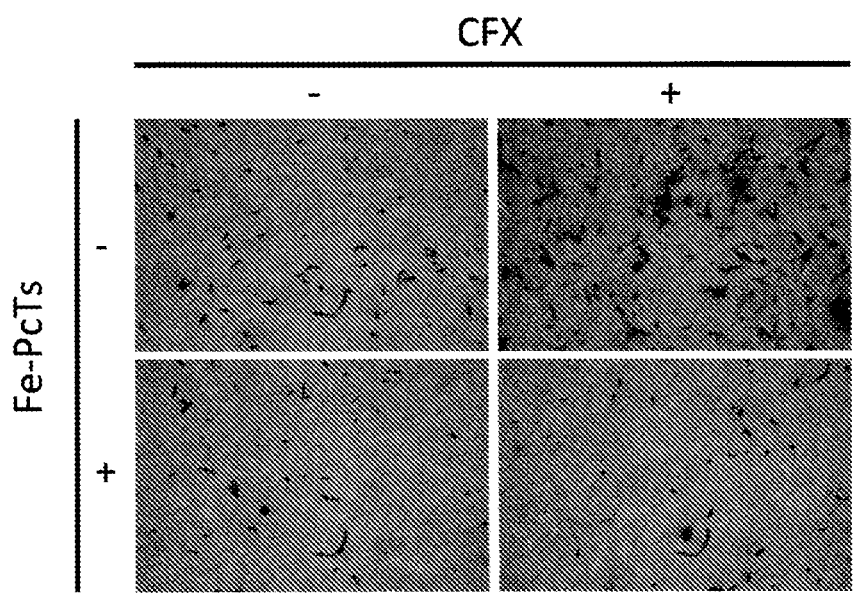
(g)
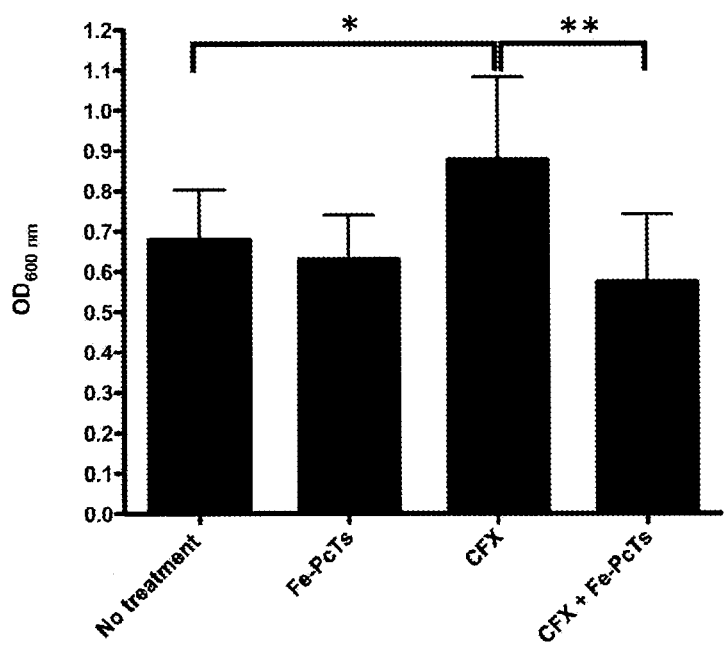

Figure 3 con't
(e)
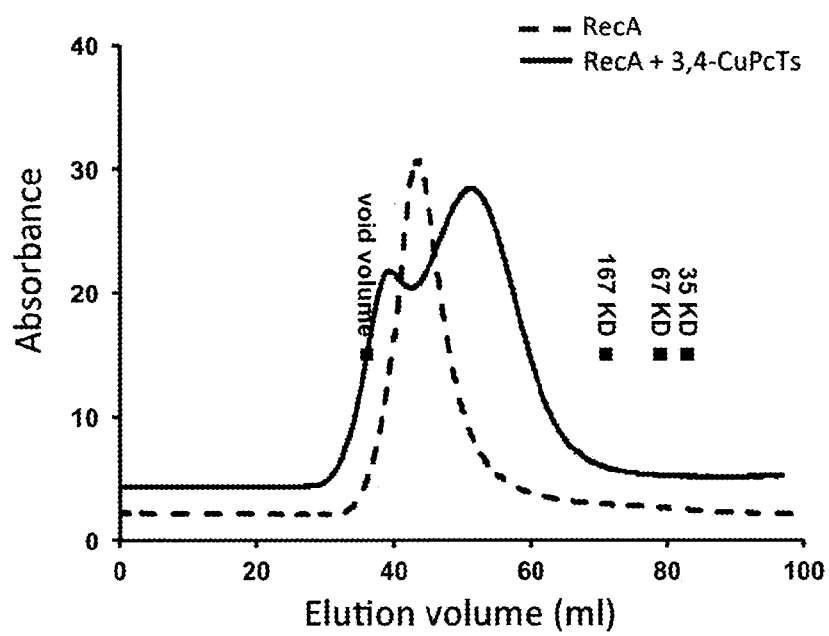
(f)
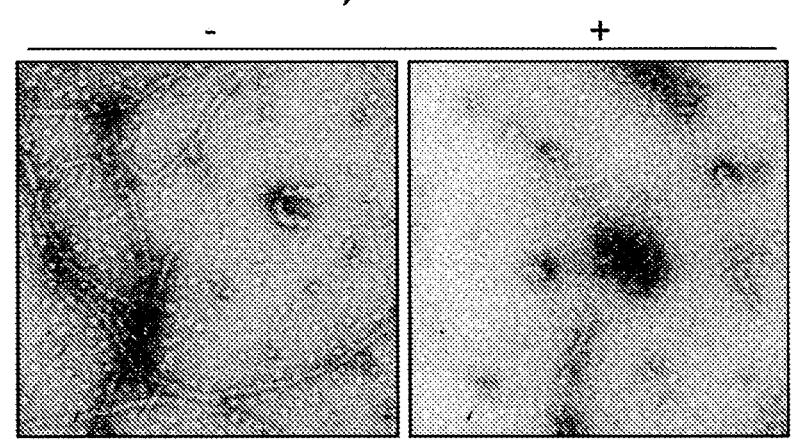

Figure 4 con't
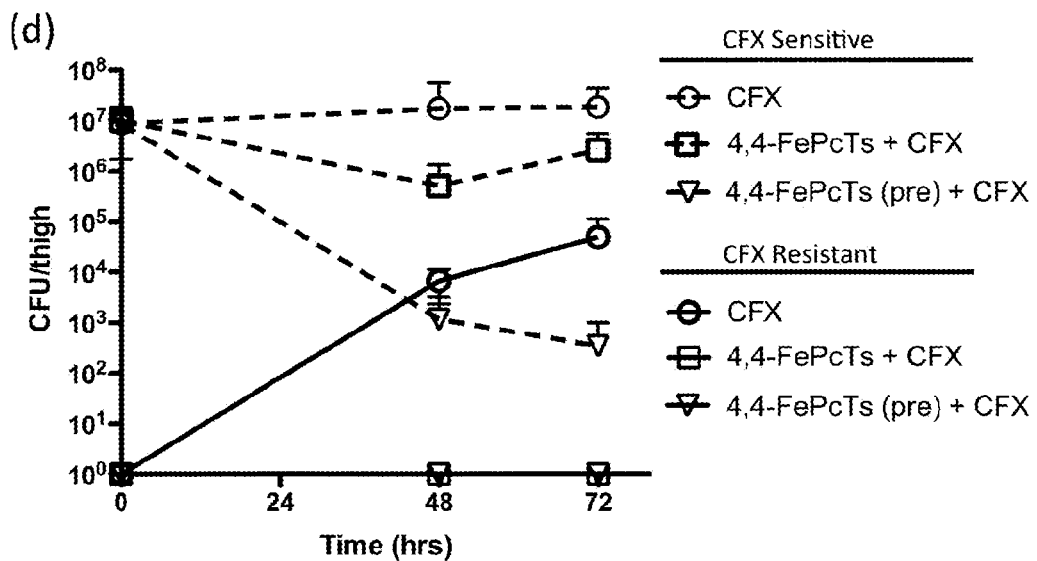
(d)
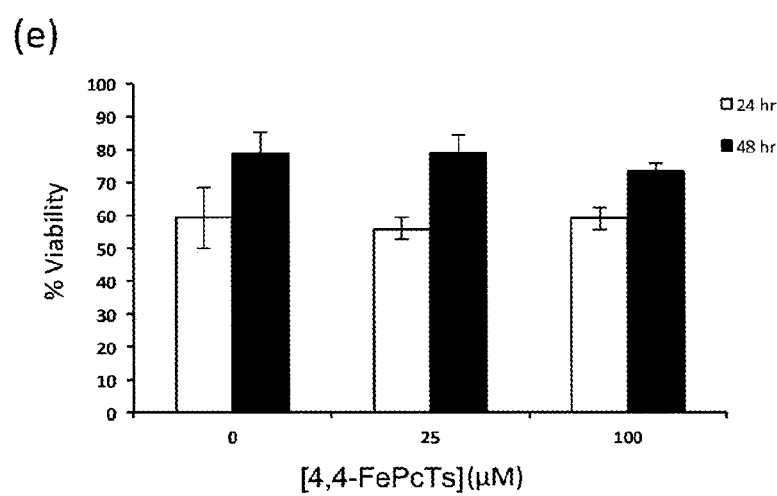
(e)

PHTHALOCYANINE COMPOUNDS USEFUL AS RECA INHIBITORS AND METHODS OF USING SAME

CROSS-REFERENCE TO RELATED APPLICATIONS

This application is a 371 of PCT/IB2013/052899, which claims priority to, and for purposes of the United States of America claims the benefit of, U.S. provisional patent application Ser. No. 61/623,493 filed 12 Apr. 2012, the entirety of which is hereby incorporated by reference herein.

TECHNICAL FIELD

Some embodiments of the present invention pertain to compounds that can be used to potentiate the effect of an antibiotic and/or to prevent or delay the onset of resistance to an antibiotic and methods of using same.

BACKGROUND

The rapid emergence of antibiotic resistance amongst pathogenic bacteria is a major clinical and public health problem. The established paradigm suggests that antibiotic resistance emerges by selecting for pre-existing mutants in the bacterial population exposed to antibiotics. However, recent data suggests that adaptive resistance mutations can occur in bacteria in response to antibiotic therapy [1, 2]. Adaptive resistance mutations may be caused by activation of the SOS DNA repair and mutagenesis pathway [3, 4]. The SOS response pathway is initiated by the accumulation of single-stranded DNA (ssDNA), promoting activation of RecA, inactivation of LexA repressor, and induction of SOS genes, including SOS error prone polymerases [5-7].

Bactericidal antibiotics are powerful instigators of the SOS response [1, 8]. Bactericidal antibiotics can induce a common mechanism of cell death by stimulating the formation of lethal amounts of oxidative radicals (hydroxyl radicals), which activates RecA and the SOS response [9]. *E. coli* strains lacking RecA are much more sensitive to bactericidal antibiotics or bacteriostatic antibiotics that are activators of the SOS response [9]. Thus, RecA can contribute to increased tolerance to antibiotic treatment by enhancing repair of DNA damage that occurs either directly by antibiotic-induced DNA damage or indirectly from metabolic and oxidative stress. RecA-mediated repair can also induce a hypermutable state that can promote acquisition of antibiotic resistance. If DNA damage is not successfully repaired, then mutagenic polymerases (PolIV and PolV) are induced, causing mutagenesis to occur and enabling bacteria to develop antibiotic resistance [1]. Bacteria can also develop antibiotic resistance by obtaining resistant genes from foreign DNA using the SOS response-mediated horizontal gene transfer pathway [10, 11].

SOS response mechanisms have also been confirmed in Gram-positive species [12]. RecA proteins, generally 318 to 388 amino acid residues in size [13], are nearly ubiquitous in bacterial species. RecA genes within protobacteria (including Gram-negative pathogens) and Gram-positive species are highly conserved [14]. Therefore, inhibitors of RecA can be used as broad-spectrum co-drugs against Gram-negative or Gram-positive pathogens.

A crystal structure of the post-ATP hydrolysis conformation of the archaebacteria *Methanococcus voltae* RecA homologue MvRadA was obtained by co-crystallizing it in the presence of ADP and the phosphate analog sodium tungstate ($Na_2WO_4$) [15]. A cluster of 12 tungsten atoms was located by outstanding anomalous scattering signals near DNA binding loops L1 and L2. The metatungstate ($W_{12}O_{40}^{6-}$) compound inhibited MvRadA ATPase, DNA-binding, and DNA strand-exchange activities [15]. This study showed that drug-sized molecules can competitively block DNA-binding by RecA-like protein filaments. However, metatungstate is unable to inhibit RecA activity within *E. coli* cells.

There remains a need for molecules that can limit the development of resistance to antibiotics.

SUMMARY

In some embodiments, an anionic phthalocyanine compound is used to potentiate the effect of an antibiotic. In some embodiments, an anionic phthalocyanine compound is used to inhibit the development of resistance to an antibiotic. In some embodiments, a subject being administered an antibiotic is administered an anionic phthalocyanine compound to potentiate the effect of the antibiotic in the subject and/or to inhibit the development of resistance to the antibiotic.

In some embodiments, a composition for potentiating the effect of an antibiotic and/or for inhibiting the development of resistance includes the antibiotic and an anionic phthalocyanine compound.

In some embodiments, the antibiotic is a DNA gyrase inhibitor or a topoisomerase inhibitor. In some embodiments, the antibiotic is a β-lactam antibiotic, an aminoglycoside antibiotic, or a quinolone antibiotic. In some embodiments, the antibiotic is ciprofloxacin, ampicillin, or kanamycin.

In some embodiments, the anionic phthalocyanine compound has the formula:

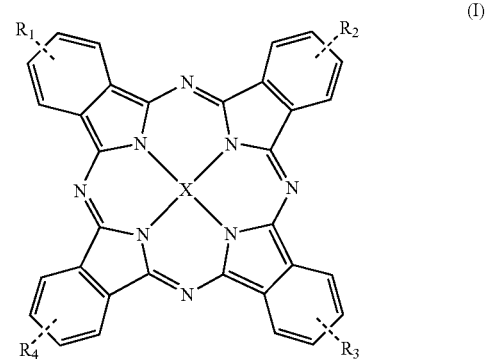

(I)

wherein X can be any element or compound that can form a coordination complex with phthalocyanine and wherein $R_1$, $R_2$, $R_3$ and $R_4$ are independently anionic moieties, or

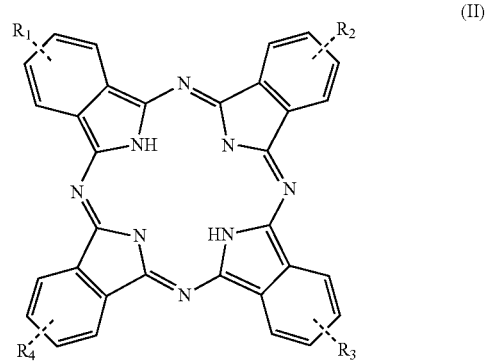

(II)

wherein $R_1$, $R_2$, $R_3$ and $R_4$ are independently anionic moieties. In some embodiments, $R_1$, $R_2$, $R_3$ and $R_4$ are —$SO_3^-$. In some embodiments, the anionic phthalocyanine compound is water soluble. In some embodiments, the anionic phthalocyanine compound is iron (III) phthalocyanine-4,4',4",4'"-tetrasulfonic acid or copper phthalocyanine-3,4',4",4'"-tetrasulfonic acid.

BRIEF DESCRIPTION OF THE DRAWINGS

FIG. 3(a) shows images of agarose gels in which RecA bound double stranded DNA (dsDNA) (slower migrating DNA) and free double stranded DNA were resolved. FIG. 3(b) shows images of agarose gels in which RecA bound single stranded DNA (ssDNA) (slower migrating DNA) and free single stranded DNA were resolved.

FIG. 3(c) shows that 4,4-Fe-PcTs and 3,4-Cu-PcTs inhibit RecA-mediated DNA strand exchange. Strand exchange activity was monitored by measuring the formation of the slowest migrating heteroduplex DNA species (FAM-labeled hdDNA) using a 36 base pair dsDNA and a 43 nucleotide FAM-labelled oligonucleotide. A native polyacrylamide gel was used to resolve the reaction products.

FIG. 3(d) shows results confirming that 4,4-Fe-PcTs and 3,4-Cu-PcTs inhibit RecA-stimulated LexA autoproteolysis. Reaction products, LexA and cleaved LexA (LexA-C) were resolved using a SDS-polyacrylamide gel and stained with Coomassie Blue.

FIG. 3(e) shows 3,4-Cu-PcTs reduces the oligomeric state of RecA. RecA complexes with or without 3,4-Cu-PcTs (50 µM) were analyzed by size exclusion chromatography. RecA eluted near the void volume of the size exclusion column. Pre-incubation with 3,4-Cu-PcTs caused the 3,4-Cu-PcTs/RecA complex to elute at ~200 KD.

FIG. 3(f) shows the formation of RecA filaments in the absence (−) and presence (+) of 3,4-Cu-PcTs. RecA, adenosine 5'-(β,γ-imido)triphosphate (AMPPNP), and dsDNA were incubated in the presence or absence of 3,4-Cu-PcTs and RecA filaments analyzed using electron microscopy.

FIG. 4(a) shows ciprofloxacin (CFX) resistant ATCC29522 cells obtained in the presence and absence of 4,4-Fe-PcTs per day. FIG. 4(b) shows viable ATCC29522 cells present on LB plates containing ciprofloxacin (CFX) or ciprofloxacin and 4,4-Fe-PcTs (CFX+4,4-Fe-PcTs) per day. FIG. 4(c) shows the number of ciprofloxacin resistant cells per viable cell per day in the presence ciprofloxacin alone (CFX) and in the presence if ciprofloxacin and 4,4-Fe-PcTs (CFX+4,4-Fe-PcTs). Error bars represent the standard deviation from two independent experiments.

FIG. 4(d) shows an in vivo analysis of the effects of 4,4-Fe-PcTs activity in a neutropenic mouse bacterial infection model. Mice were infected with ATCC25922 cells and treated with CFX or CFX and Fe-PcTs. Fe-PcTs was either administered 24 hours before CFX treatment (pre) or co-administered with CFX. Mice were sacrificed at 48 and 72 hours and ATCC25922 cells from mice thighs were cultured on LB plates with or without CFX (40 nM) to determine the number of CFX sensitive (dashed lines) and CFX resistant (solid lines) ATCC25922 CFUs. Error bars represent standard deviation from five independent experiments.

FIG. 4(e) shows the viability of mouse bone marrow cells treated with indicated concentrations of 4,4-Fe-PcTs for 24 and 48 hours. Error bars represent the standard deviation from three independent experiments.

DETAILED DESCRIPTION

Figure 1:
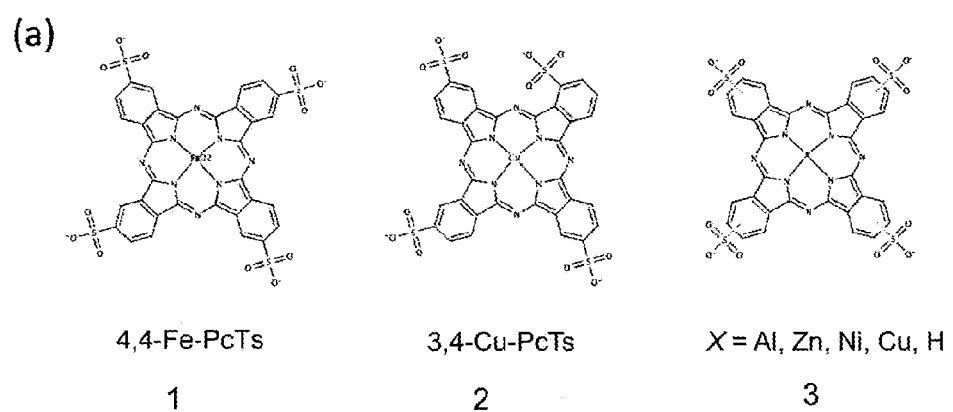
FIG. 1(a) shows the structures of the following phthalocyanine tetrasulfonic acid-based inhibitors: iron (III) phthalocyanine-4,4',4",4'"-tetrasulfonic acid (4,4-Fe-PcTs) (1), copper phthalocyanine-3,4',4",4'"-tetrasulfonic acid (3,4-Cu-PcTs) (2), and X-PcTs molecules incorporating mixtures of different sulfonic acid regioisomers (3) (wherein X represents Al, Zn, Ni, Cu or H).
FIG. 1(b) shows relative inhibition of poly-$(dT)_{36}$-stimulated RecA ATPase activity by 4,4-Fe-PcTs and 3,4-Cu-PcTs relative to activity in the absence of RecA inhibitor. DltA was assayed in the presence of 3,4-Cu-PcTs as a control.
FIG. 1(c) shows the potentiation of ciprofloxacin activity by 4,4-Fe-PcTs and 3,4-Cu-PcTs. ATCC25922 cells were treated with ciprofloxacin (40 nM: dashed lines) or ciprofloxacin at 40 nM plus the indicated concentrations of 4,4-Fe-PcTs or 3,4-Cu-PcTs. CFUs/ml were determined at indicated time points.
FIG. 1(d) shows a comparison of the potentiation of ciprofloxacin by different phthalocyanine tetrasulfonic acid molecules. ATCC25922 cells were treated with ciprofloxacin (40 nM: Con) or ciprofloxacin (40 nM) plus the indicated phthalocyanine tetrasulfonic acid molecules (25 µM). CFUs/ml were determined at 24 hours. Error bars in FIGS. 1(c) and 1(d) represent the standard deviation from three independent experiments.
Figure 1:
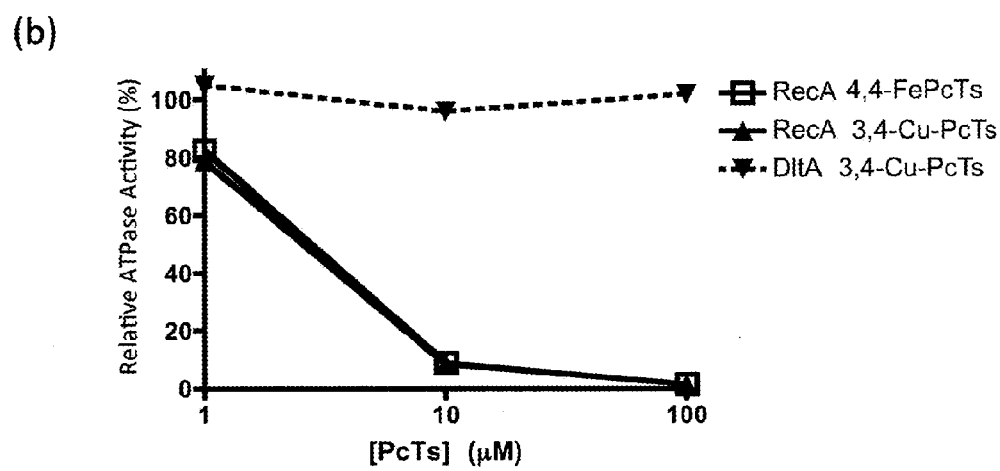

A number of studies exist connecting antibiotic activity to the activation of the SOS response and showing the induction of antibiotic resistance mutations by the SOS response. Such studies demonstrate that there is potential to potentiate the effect of antibiotics and/or prevent the development of antibiotic resistance by targeting proteins essential for the SOS response. Without being bound by any theory or mechanism of action, the link between bactericidal antibiotics and the induction of the SOS response [1, 9] suggests that the acquisition of antibiotic resistance can be linked to antibiotic-mediated DNA damage [1] (e.g. DNA damage caused directly by antibiotics, or caused indirectly due to metabolic and/or oxidative stress) and the formation of RecA-ssDNA filaments, which are key intermediates in DNA repair mechanisms and the SOS response.

RecA-mediated repair induces a hypermutable state that promotes the acquisition of mutations in genes that cause resistance. If repair of DNA damage is not successful, then RecA-ssDNA filaments persist and degrade enough LexA to allow late response SOS genes to be induced, which encode mutagenic polymerases (PolIV and PolV). Expression of these polymerases causes mutations in genes that can enable the development of resistance [1]. RecA is also involved in the chromosomal integration of exogenous DNA in the SOS response, facilitating horizontal gene transfer, which can result in the transfer of genes conferring antibiotic resistance between microorganisms.

Based on the role of RecA in the SOS response and the fact that strains lacking RecA are more sensitive to antibiotics, RecA was targeted for antibiotic therapy to prevent induction of SOS response and/or block antibiotic-induced DNA repair and mutagenesis.

Some embodiments of the present invention provide anionic phthalocyanine compounds that can potentiate the efficacy of antibiotics and/or inhibit the acquisition of resistance to such antibiotics by bacteria or other microorganisms. In some embodiments, the anionic phthalocyanine compounds are phthalocyanine tetrasulfonic acid (abbreviated "PcTs") compounds. Without being bound by a mechanism of action, the anionic phthalocyanine compounds act as inhibitors of RecA that can block antibiotic-induced activation of the SOS response.

In principle, RecA can be inhibited by targeting three functionally important processes: recruitment and polymerization, ATP binding, and DNA binding. These processes are connected by allosteric regulatory mechanisms and are difficult to differentiate biochemically from each other. The inventors have demonstrated that anionic phthalocyanine compounds block the ATPase, DNA-binding, DNA strand-exchange, and LexA proteolysis activities of RecA. Anionic phthalocyanine compounds potentiate the activity of antibiotics that are activators of the SOS response and reduce the ability of bacteria to acquire antibiotic resistance mutations.

As used herein, the term "bactericidal antibiotics" refers to antibiotics that act by killing bacteria. Exemplary bactericidal antibiotics include aminoglycosides such as amikacin, arbekacin, apramycin, gentamicin, kanamycin, neomycin, netilmicin, paromomycin, streptomycin, rhodostreptomycin, tobramycin; aminocoumarins such as novobiocin, coumermycin, clorobiocin; ansamycins such as geldanamycin, herbimycin; carbacephems such as loracarbef; carbapenems such as ertapenem, doripenem, imipenem, meropenem; cephalosporins such as cefadroxil, cefazolin, cefalotin, cefalexin, cefector, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole; lipopeptides such as daptomycin; monobactams such as aztreonam; penicillins such as amdinocillin, amoxicillin, ampicillin, azlocillin, bacampicillin, benzathine, carbenicillin, cloxacillin, cyclacillin, dicloxacillin, flucloxacillin, mezlocillin, methicillin, nafcillin, oxacillin, penicillin G, penicillin V, piperacillin, temocillin, ticarcillin and other β-lactam antibiotics; nitrofurans such as furazolidone, nitrofurantoin; polypeptides such as bacitracin, colistin, polymyxin B; quinolones and fluoroquinolones such as ciprofloxacin, enoxacin, gatifloxacin, levofloxacin, lomefloxacin, moxifloxacin, nalidixic acid, norfloxacin, ofloxacin, trovafloxacin, grepafloxacin, gemifloxacin, sparfloxacin, temafloxacin; vancomycin, metronidazole, co-trimoxazole, telithromycin, clofazimine, dapsone, cycloserine, pyrazinamide, rifampicin, rifabutin, and the like.

The term "bactericidal antibiotics" as used herein also includes antibiotics that may be developed in the future and which act by killing bacteria.

"Bacteriostatic antibiotics" refers to antibiotics that act by slowing the rate of growth or reproduction of bacteria. Exemplary bacteriostatic antibiotics include tetracyclines such as demeclocycline, doxycycline, minocycline, oxytetracycline, tetracycline; sulfonamides such as mafenide, sulfonamidochrysoidine, sulfacetamid, sulfadiazine, sulfamethizole, sulfamethoxazole, sulfanilamide, sulfsalazine, slufisoxazole, trimethoprim; spectinomycin; chloramphenicol; lincosamides such as clindamycin, lincomycin; glycopeptides such as vancomycin, teicoplanin, telavancin, bleomycin, ramoplanin, decaplanin (glycopeptides are bactericidal against enterococci); macrolides such as azithromycin, clarithromycin, dirithromycin, erythromycin, roxithromycin, troleandomycin, telithromycin, spectinomycin; streptogramins such as pristinamycin, dalfopristin and quinupristin; trimethoprim, capreomycin, ethambutol, fusidic acid, tigecycline, and the like. The term "bacteriostatic antibiotics" as used herein also includes antibiotics that may be developed in the future and which act by slowing the rate of growth or reproduction of bacteria.

In some cases, a given antibiotic can act as a bacteriostatic antibiotic under some conditions, and a bactericidal antibiotic under other conditions. For example, many bacteriostatic antibiotics can become bactericidal depending on their concentration, co-treatment with other drugs, or the species of bacteria in which they are used [16]. The term "bactericidal antibiotic" encompasses the use of such antibiotics in those species in or under conditions at which the antibiotic has a bactericidal effect. In some cases, a given antibiotic can act as a bacteriostatic antibiotic at lower concentrations, and as a bactericidal antibiotic at higher concentrations. The term "bactericidal antibiotic" encompasses the use of such antibiotics at concentrations or doses at which the antibiotic has a bactericidal effect.

As used herein, "antibiotic that is an activator of the SOS response" means an antibiotic that induces the SOS response pathway in bacteria. Most if not all bactericidal antibiotics will be activators of the SOS response (see e.g. [9]). Additionally, some bacteriostatic antibiotics can also act as activators of the SOS response, particularly in higher concentrations. The term "antibiotic that is an activator of the SOS response" includes those antibiotics that produce an increase above a measured basal level of SOS induction when bacteria are exposed to the antibiotic. In some embodiments, an antibiotic that is an activator of the SOS response produces at least a 10% increase in the induction of SOS response, including e.g. a 20%, 30%, 40%, 50%, 60%, 70%, 80%, 90%, 100%, five-fold, ten-fold, twenty-fold or one hundred-fold increase in the induction of SOS response, as measured by expression of GFP regulated by the sulA SOS promoter, e.g. using methods described in [17].

Bacteriostatic antibiotics tend not to activate the SOS response [9]. One exception is rifamycin. Rifamycin is considered to be a bacteriostatic antibiotic. Rifamycin activates the SOS response, but does not kill bacteria [9]. However, in a ΔrecA bacterial strain, rifamycin shows bactericidal activity [9]. Thus, a bacteriostatic antibiotic that activates the SOS response can kill bacteria in which RecA has been deleted, which supports that bacteriostatic antibiotics that activate the SOS response, including rifamycin, can yield bactericidal activity if administered together with an inhibitor of RecA.

"Potentiate" means that a compound does one or more of: increasing the effectiveness of an antibiotic, decreasing a dose of an antibiotic required to kill bacteria or limit bacterial growth, or rendering a bacteria that would otherwise be resistant to an antibiotic sensitive to that antibiotic. In some embodiments, a compound potentiates the effect of an antibiotic if it increases the effectiveness of the antibiotic by 10% or more, or decreases the dose of an antibiotic required to kill bacteria or limit bacterial growth by 10% or more.

As used herein, "inhibiting development of antibiotic resistance" means preventing antibiotic resistance from arising or slowing the rate of development of resistance to an antibiotic (i.e. delaying the emergence of resistance to an antibiotic).

"Infection" means that a subject is suffering from the presence of a higher number of one or more microorganisms than would be expected in a healthy subject. An infection may be localized (restricted to a particular region, organ, system or the like of the subject) or systemic (affecting a number of regions, organs, systems or the like of the subject). Exemplary types of infections that may be treated by antibiotics include anthrax (*Bacillus anthracis*), lyme disease (*Borrelia burgdorferi*), brucellosis (*Brucella* spp.), enteritis (*Campylobacter jejuni*), *Clostridium difficile* infections, *Clostridium perfringens* infections, diphtheria (*Corynebacterium diphtheriae*), nosocomial infections (e.g. caused by *Enterococcus faecalis* or *Enterococcus faecium*), *Escherichia coli* infections (including by Enterotoxigenic *E. coli* or Enteropathogenic *E. coli*), tularemia (*Francisella tularensis*), *Haemophilus influenzae* infections, *Helicobacter pylori* infections, Legionnaire's disease (*Legionella pneumophila*), leptospirosis (*Leptospira interrogans*), listeriosis (*Listeria monocytogenes*), leprosy (*Mycobacterium leprae*), tuberculosis (*Mycobacterium tuberculosis*), gonorrhea (*Neisseria gonorrhoeae*), meningococcal disease (*Neisseria meningitides*), pseudomonas infection (*Pseudomonas aeruginosa*), typhoid fever or salmonellosis (*Salmonella typhi, Salmonella typhimurium*), shigellosis (*Shigella sonnei*), staphylococcal infections (*Staphylococcus aureus, Staphylococcus epidermis, Staphylococcus saprophyticus*), streptococcus infections (*Streptococcus agalactiae, Streptococcus pneumoniae, Streptococcus pyogenes*), syphilis (*Treponema pallidum*), plague (*Yersinia pestis*), or the like. In some embodiments, the infection is a bacterial infection. In some embodiments, the infection is caused by a combination of a bacterial infection and an infection with one or more other types of microorganisms.

"Subject" means an organism to which an antibiotic is to be administered. In some embodiments, the subject is suffering from an infection. In some embodiments, the subject is a mammal. In some embodiments, the subject is a human. In some embodiments, the subject is livestock, i.e. an animal raised in an agricultural setting to provide food, fiber or labour. In some embodiments, the subject is a domesticated animal. In some embodiments, the subject is a horse, mule, donkey, cow, buffalo, llama, alpaca, sheep, goat, pig, dog, cat, rabbit, mouse or rat.

As used herein, "anionic phthalocyanine compound" means a phthalocyanine compound having functional groups that have a high probability of being negatively charged (i.e. anionic) at physiological pH. For example, a carboxylic acid functional group can exist in two different forms, either the protonated (uncharged) form —CO(OH) or the unprotonated (negatively charged) form —$CO_2^-$, together with an appropriate counterion. At low pH, the protonated (uncharged) form of the carboxylic acid will be the preferred form. At physiological pH, the unprotonated (negatively charged) form will be the preferred form. Thus, the term "anionic phthalocyanine compound" is not restricted to compounds that are negatively charged under all possible conditions, and further is intended to encompass compounds that are protonated and/or accompanied by appropriate counterions. In some embodiments, the anionic phthalocyanine compound is water-soluble.

In some embodiments, an anionic phthalocyanine compound having the general structure

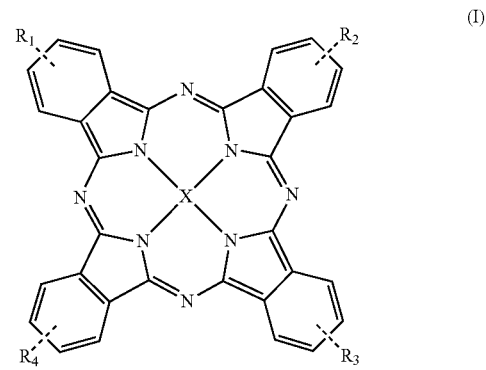

(I)

is provided, wherein X can be any element or compound that forms a coordination complex with phthalocyanine, and $R_1$, $R_2$, $R_3$ and $R_4$ are independently anionic moieties such as a sulfonate group (—$SO_3^-$), sulfate group (—$OSO_3^-$), carboxylate group (—$CO_2^-$), a phosphate group (—$OHPO_3^-$), a phosphonate group (—HPO$_3^-$), a nitrate group (—ONO$_2^-$), a nitro group (—NO$_2^-$) or the like. In some embodiments, such compound is used as an agent to potentiate the effect of an antibiotic. In some embodiments, an anionic phthalocyanine compound having the general structure (I), wherein X can be any element or compound that forms a coordination complex with phthalocyanine and wherein R$_1$, R$_2$, R$_3$ and R$_4$ are independently anionic moieties such as a sulfonate group (—SO$_3^-$), sulfate group (—OSO$_3^-$), carboxylate group (—CO$_2^-$), a phosphate group (—OHPO$_3^-$), a phosphonate group (—HPO$_3^-$), a nitrate group (—ONO$_2^-$), a nitro group (—NO$_2^-$) or the like, is used as an agent to inhibit the development of bacterial resistance to an antibiotic. In some embodiments, X is FeO$_2$, Cu, Al, Zn or Ni. In some embodiments, the anionic phthalocyanine compound is a phthalocyanine tetrasulfonic acid compound, i.e. R$_1$, R$_2$, R$_3$ and R$_4$ are —SO$_3^-$. In some embodiments, the phthalocyanine tetrasulfonic acid compound is iron (III) phthalocyanine-4,4',4'',4'''-tetrasulfonic acid or copper phthalocyanine-3,4',4'',4'''-tetrasulfonic acid.

Exemplary compounds and elements that can form a coordination complex with phthalocyanine, and methods of synthesizing such coordination complexes, are described, for example, in Neil B. McKeown, *Phthalocyanine Materials Synthesis, Structure and Function*, University of Manchester Hardback Series: Chemistry of Solid State Materials (No. 6), 1998 (ISBN:9780521496230), which is hereby incorporated by reference herein for all purposes. Methods of synthesizing anionic phthalocyanines are described, for example, in Dumoulin et al., *Coord. Chem. Rev.* 254: 2792-2847 (2010), which is hereby incorporated by reference herein for all purposes.

In some embodiments, an anionic phthalocyanine compound having the structure

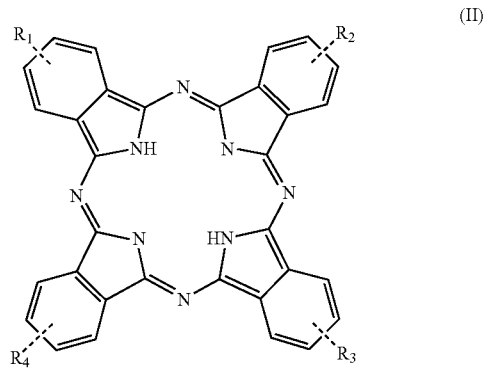

(II)

wherein R$_1$, R$_2$, R$_3$ and R$_4$ are independently anionic moieties such as a sulfonate group (—SO$_3^-$), a sulfate group (—OSO$_3^-$), a carboxylate group (—CO$_2^-$), a phosphate group (—OHPO$_3^-$), a phosphonate group (—HPO$_3^-$), a nitrate group (—ONO$_2^-$), a nitro group (—NO$_2^-$) or the like, is used as an agent to potentiate the effect of an antibiotic. In some embodiments, an anionic phthalocyanine compound having the general structure (II) is used as an agent to inhibit the development of bacterial resistance to an antibiotic. In some embodiments, the anionic phthalocyanine compound is a phthalocyanine tetrasulfonic acid compound, i.e. R$_1$, R$_2$, R$_3$ and R$_4$ are —SO$_3^-$. In some embodiments, the phthalocyanine tetrasulfonic acid compound is a 3,4',4'',4'''-phthalocyanine tetrasulfonic acid compound. In some embodiments, the phthalocyanine tetrasulfonic acid compound is a 4,4',4'',4'''-phthalocyanine tetrasulfonic acid compound.

In some embodiments, an anionic phthalocyanine compound is administered to a subject in conjunction with an antibiotic. In some embodiments, the anionic phthalocyanine compound is administered to a subject in conjunction with an antibiotic to potentiate the effect of the antibiotic and/or to inhibit the development of resistance to the antibiotic in the subject.

In some embodiments, the anionic phthalocyanine compound is administered concurrently with (i.e. at approximately the same time as) the antibiotic. In some embodiments, the anionic phthalocyanine compound is administered separately from (i.e. at a different time than) the antibiotic. In some embodiments, the anionic phthalocyanine compound is administered prior to administration of an antibiotic. In some embodiments, the anionic phthalocyanine compound is administered after administration of an antibiotic. In embodiments in which the anionic phthalocyanine compound and the antibiotic are not administered concurrently, the anionic phthalocyanine compound and the antibiotic should be administered sufficiently close in time that a significant proportion (e.g. greater than 50%) of each compound remains in its active state while both the antibiotic and the anionic phthalocyanine compound are in the subject's system.

The antibiotic and the anionic phthalocyanine compound can be administered in any suitable manner, and need not both be administered in the same manner. In some embodiments, the antibiotic and/or the anionic phthalocyanine are administered orally. Suitable methods of administration can be selected by one skilled in the art, and include topical administration, injection or delivery to a desired location (including intravenous or intramuscular injection), or the like. In some embodiments, the antibiotic and/or the anionic phthalocyanine are administered by oral, parenteral, cutaneous, rectal, nasal, or vaginal administration.

In some embodiments, the antibiotic is administered at a daily dosage in the range of 0.1 mg/kg to 10 mg/kg. In some embodiments, the anionic phthalocyanine compound is administered at a daily dosage in the range of 1 mg/kg to 20 mg/kg. In some embodiments, the antibiotic is administered at a daily dosage of about 1 mg/kg and the anionic phthalocyanine compound is administered at a daily dosage in the range of about 10 mg/kg.

In some embodiments, the invention provides a composition including an antibiotic and an anionic phthalocyanine compound for potentiating the effect of an antibiotic. In some embodiments, the invention provides a composition including an antibiotic and an anionic phthalocyanine compound for inhibiting the development of antibiotic resistance. In some embodiments, the composition includes a pharmaceutically effective amount of the antibiotic and a pharmaceutically effective amount of the anionic phthalocyanine compound.

In some embodiments, the composition includes a pharmaceutically acceptable derivative, salt, metabolite or structural or functional analogue of the antibiotic. In some embodiments, the composition includes a pharmaceutically acceptable derivative, salt, metabolite, or structural or functional analogue of the anionic phthalocyanine compound.

In some embodiments, the composition includes a pharmaceutically acceptable carrier. In some embodiments, the composition includes a pharmaceutically effective amount of the antibiotic and a pharmaceutically effective amount of the anionic phthalocyanine compound.

In some embodiments, the invention provides a dosage form that includes an antibiotic and an anionic phthalocyanine compound. In some embodiments, the dosage form is a tablet, capsule, granule, powder, syrup, suspension, emulsion, solution, gel, paste, ointment, cream, lotion, plaster, skin patch, drench, suppository, enema, injectable solution, implant, spray or aerosol.

In some embodiments, the dosage form includes a pharmaceutically acceptable carrier. In some embodiments, the dosage form includes a pharmaceutically effective amount of the antibiotic and a pharmaceutically effective amount of the anionic phthalocyanine compound. In some embodiments, the dosage form includes between 1 and 1000 mg of the antibiotic. In some embodiments, the dosage form includes between 10 and 2000 mg of the anionic phthalocyanine compound.

In some embodiments, the antibiotic is an antibiotic that is an activator of the SOS response. In some embodiments, the antibiotic is a bactericidal antibiotic. In some embodiments, the antibiotic is a bacteriostatic antibiotic that is an activator of the SOS response, for example, rifamycin. In some embodiments, the antibiotic is a bacteriostatic antibiotic used at a sufficiently high concentration or dosage to activate the SOS response or act as a bactericidal antibiotic; that is used in a species in which the bacteriostatic antibiotic activates the SOS response or acts as a bactericidal antibiotic; or that is co-administered together with an agent that causes the bacteriostatic antibiotic to act as a bactericidal antibiotic or activate the SOS response. In some embodiments, the antibiotic is a bactericidal antibiotic that acts by causing DNA damage. In some embodiments, the antibiotic is a DNA gyrase inhibitor, a topoisomerase inhibitor, or the like. DNA gyrase is a type II topoisomerase. Exemplary antibiotics that are DNA gyrase inhibitors include quinolones, aminocoumarins, and the like. Exemplary antibiotics that are topoisomerase IV inhibitors include quinolones and fluoroquinolones.

In some embodiments, the antibiotic is an aminoglycoside such as amikacin, arbekacin, apramycin, gentamicin, kanamycin, neomycin, netilmicin, paromomycin, streptomycin, rhodostreptomycin, tobramycin; an aminocoumarin such as novobiocin, coumermycin, clorobiocin; an ansamycin such as geldanamycin, herbimycin; a carbacephem such as loracarbef; a carbapenem such as ertapenem, doripenem, imipenem, meropenem; a cephalosporin such as cefadroxil, cefazolin, cefalotin, cefalexin, cefector, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole; a lipopeptide such as daptomycin; a monobactam such as aztreonam; a nitrofuran such as furazolidone, nitrofurantoin; a penicillin such as amdinocillin, amoxicillin, ampicillin, azlocillin, bacampicillin, benzathine, carbenicillin, cloxacillin, cyclacillin, dicloxacillin, flucloxacillin, mezlocillin, methicillin, nafcillin, oxacillin, penicillin G, penicillin V, piperacillin, temocillin, ticarcillin; another β-lactam antibiotic; a polypeptide such as bacitracin, colistin, polymyxin B; a quinolone or fluoroquinolone such as ciprofloxacin, enoxacin, gatifloxacin, levofloxacin, lomefloxacin, moxifloxacin, nalidixic acid, norfloxacin, ofloxacin, trovafloxacin, grepafloxacin, gemifloxacin, sparfloxacin, temafloxacin; vancomycin, metronidazole, co-trimoxazole, telithromycin, clofazimine, dapsone, cycloserine, pyrazinamide, rifampicin, rifabutin, or the like.

In some embodiments, the antibiotic is a tetracycline such as demeclocycline, doxycycline, minocycline, oxytetracycline, tetracycline; a sulfonamide such as mafenide, sulfonamidochrysoidine, sulfacetamid, sulfadiazine, sulfamethizole, sulfamethoxazole, sulfanilamide, sulfsalazine, slufisoxazole, trimethoprim; spectinomycin; chloramphenicol; a lincosamide such as clindamycin, lincomycin; a glycopeptide such as vancomycin, teicoplanin, telavancin, bleomycin, ramoplanin, decaplanin; a macrolide such as azithromycin, clarithromycin, dirithromycin, erythromycin, roxithromycin, troleandomycin, telithromycin, spectinomycin; a streptogramin such as pristinamycin, dalfopristin, quinupristin; trimethoprim, capreomycin, ethambutol, fusidic acid, tigecycline, or the like.

In some embodiments, any of the methods, compositions or dosage forms described above are used to treat a microbial infection. In some embodiments, the microbial infection is a bacterial infection. In some embodiments, the methods, compositions or dosage forms described above are used to treat conditions that are typically treated by antibiotics, including for example anthrax (*Bacillus anthracis*), lyme disease (*Borrelia burgdorferi*), brucellosis (*Brucella* spp.), enteritis (*Campylobacter jejuni*), *Clostridium difficile* infections, *Clostridium perfringens* infections, diphtheria (*Corynebacterium diphtheriae*), nosocomial infections (e.g. caused by *Enterococcus faecalis* or *Enterococcus faecium*), *Escherichia coli* infections (including by Enterotoxigenic *E. coli* or Enteropathogenic *E. coli*), tularemia (*Francisella tularensis*), *Haemophilus influenzae* infections, *Helicobacter pylori* infections, Legionnaire's disease (*Legionella pneumophila*), leptospirosis (*Leptospira interrogans*), listeriosis (*Listeria monocytogenes*), leprosy (*Mycobacterium leprae*), tuberculosis (*Mycobacterium tuberculosis*), gonorrhea (*Neisseria gonorrhoeae*), meningococcal disease (*Neisseria meningitides*), pseudomonas infection (*Pseudomonas aeruginosa*), typhoid fever or salmonellosis (*Salmonella typhi*, *Salmonella typhimurium*), shigellosis (*Shigella sonnei*), staphylococcal infections (*Staphylococcus aureus*, *Staphylococcus epidermis*, *Staphylococcus saprophyticus*), streptococcus infections (*Streptococcus agalactiae*, *Streptococcus pneumoniae*, *Streptococcus pyogenes*), syphilis (*Treponema pallidum*), plague (*Yersinia pestis*), or the like. In some embodiments, more than one antibiotic is used or administered to a subject together with one or more anionic phthalocyanine compounds.

In some embodiments, any of the methods, compositions or dosage forms described above are targeted at a Gram positive bacteria. In some embodiments, any of the methods, compositions or dosage forms described above are targeted at a Gram negative bacteria.

EXAMPLES

Embodiments of the invention are further described with reference to the following examples, which are intended to be illustrative and not restrictive in nature.

Example 1

General Materials and Methods

Protein Expression and Purification:

Chemicals for protein purification were purchased from VWR unless specified otherwise. pET28a plasmids containing *E. coli* RecA and LexA coding sequences (EcRecA & EcLexA) were transfected into the BL21(DE3) *E. coli* strain. Recombinant RecA and LexA proteins containing an N-terminal histidine tag were overexpressed by inducing the culture with 0.5 mM IPTG for four hours. Cells were lysed and histidine-tagged proteins were purified by metal-affinity chromatography and gel filtration chromatography. Purified proteins were concentrated to ~10 mg/ml by ultra-filtration and stored at −80° C.

Bacterial Strains:

The following strains were obtained from ATCC. Gram Negative: *Escherichia coli* ATCC25922, *Pseudomonas aeruginosa* ATCC27853. Gram positive: *Staphylococcus aureus* ATCC29213, and *Enterococcus faecalis* ATCC29212. *Escherichia coli* K-12 strain with a LexA regulated GFP reporter gene (strain SS996) was constructed by Susan Rosenberg [17].

Media and Antibiotics:

Experiments for ATCC25922 and SS996 were performed in Luria-Bertani (LB) broth or LB agar plates (Difco). Experiments for ATCC27853, ATCC29212, and ATCC292123 were performed in Mueller-Hinton broth (MH) or in tryptic soy blood agar plates. The following antibiotics were used: ampicillin (Shelton Scientific), kanamycin monosulfate (Sigma), ciprofloxacin hydrochloride (Bayer), chloramphenicol (Sigma), tetracycline (Fluka), and spectinomycin dihydrochloride (Sigma). The following phthalocyanines were used: iron (III) phthalocyanine-4,4',4'',4'''-tetrasulfonic acid (4,4-Fe-PcTs) (Sigma), copper phthalocyanine-3,4',4'',4'''-tetrasulfonic acid tetrasodium salt (3,4-Cu-PcTs) (Sigma), phthalocyanine tetrasulfonic acid (H-PcTs) (Sigma), aluminum (III) phthalocyanine chloride tetrasulfonic acid (Al-PcTs) (Frontier Scientific), zinc (II) phthalocyanine tetrasulfonic acid (Zn-PcTs) (Frontier Scientific), nickel (II) phthalocyanine-tetrasulfonic acid (Ni-PcTs) (Sigma), and copper phthalocyanine-tetrasulfonic acid (Cu-PcTs) (Sigma).

Antibiotic Sensitivity Assays:

Bacterial cultures were diluted to $10^5$ cells/mL in LB broth (ATCC25922) or MH broth (ATCC27853, ATCC29212, ATCC29213). Antibiotics and/or phthalocyanines were added at indicated concentrations and the culture was incubated at 37° C. Samples were collected at 0, 24, 48, and 72 hours and plated on LB agar (ATCC25922) or tryptic soy blood agar (ATCC27853, ATCC29212, ATCC29213) to determine CFUs/ml.

Example 2

Identification of Inhibitors of RecA ATPase Activity

An ATPase assay [18] was used to screen a set of commercially available anionic, aromatic molecules for inhibitors of RecA ATPase activity. The release of inorganic phosphate by ATP hydrolysis was monitored using a Malachite Green phosphate assay [18]. The ssDNA-dependent ATPase reaction contained 1 µM EcRecA, 6 µM ssDNA (poly-(dT)$_{36}$, concentration in nucleotides), 5 mM ATP, 50 mM Tris-Hepes buffer at pH 7.4, 10 mM MgCl$_2$, 0.1% v/v 2-mercaptoethanol, and indicated amounts of 4,4-Fe-PcTs or 3,4-Cu-PcTs. Phosphate levels were measured by transferring 25 µl of ATPase reaction to 475 µl of malachite green phosphate assay, which contained 0.033% w/v Malachite Green, 1.3% w/v ammonium molybdate. 1.0 M HCl was used to monitor the release of inorganic phosphate by ATP hydrolysis [18]. The green complex formed between Malachite Green, molybdate, and free orthophosphate was measured by recording the absorbance at 620 nm.

From this screen, two phthalocyanine tetrasulfonic acid compounds, copper phthalocyanine-3,4',4'',4'''-tetrasulfonic acid (3,4-Cu-PcTs) (structure 1) and iron (III) phthalocyanine-4,4',4'',4'''-tetrasulfonic acid (4,4-Fe-PcTs) (structure 2), were identified (FIG. 1(*a*)). Both compounds showed a high degree of inhibition of EcRecA ATPase activity at a concentration of 10 µM (results shown in FIG. 1(*b*)). The percentage of ATPase activity is reported relative to the reaction in the absence of RecA inhibitor. DltA was used as a control to show that the 3,4-Cu-PcTs was specific for inhibiting RecA ATPase activity. DltA catalyzes the breakdown of ATP into AMP and pyrophosphate, which is further broken down by yeast pyrophosphatase into phosphate for quantification. Results are the average of two independent experiments where the deviation was less than 10%.

Example 3

Evaluation of Potentiation of Antibiotic Activity of Ciprofloxacin by Phthalocyanine Tetrasulfonic Acid Compounds The ability of 4,4-Fe-PcTs and 3,4-Cu-PcTs to potentiate the activity of ciprofloxacin (abbreviated "CFX") was tested. Ciprofloxacin inhibits DNA gyrase in bacteria, causing accumulation of double-stranded DNA breaks (DSBs) and inducing the SOS response [19]. The inventors characterized the ability of 4,4-Fe-PcTs and 3,4-Cu-PcTs to potentiate the activity of ciprofloxacin in the pathogenic *E. coli* strain ATCC25922, which was used previously by Cirz et al. to evaluate the role of SOS response proteins in antibiotic resistance [1].

4,4-Fe-PcTs and 3,4-Cu-PcTs potentiated the activity of ciprofloxacin (at a concentration of 40 nM), and no colony forming units (CFUs) were observed when ATCC25922 cells were co-treated with ciprofloxacin (40 nM) and Fe-PcTs or 3,4-Cu-PcTs at concentrations above 25 µM (FIG. 1(*c*)).

Example 4

Evaluation of Sulfonic Acid Position in Potentiating Antibiotic Activity

The importance of sulfonic acid position in the ciprofloxacin potentiating activity of 3,4-Cu-PcTs was evaluated. The ciprofloxacin potentiating activity of 3,4-Cu-PcTs was compared with that of copper phthalocyanine-tetrasulfonic acid (Cu-PcTs), which contains a mixture of sulfonic acid regioisomers. Treatment of ATCC25922 cells with Cu-PcTs (25 µM) and ciprofloxacin (40 nM) caused an ~100-fold decrease in CFUs relative to ciprofloxacin treatment alone (40 nM), which was substantially lower than 3,4-Cu-PcTs (25 µM) plus ciprofloxacin (40 nM), where no CFUs were observed (FIG. 1(*d*)).

Example 5

Evaluation of Chelated Metal in Potentiating Antibiotic Activity

To determine the importance of the metal ion chelated to the phthalocyanine tetrasulfonic acid compound, the ciprofloxacin potentiating activity of the following phthalocyanine tetrasulfonic acid molecules was evaluated: phthalocyanine tetrasulfonic acid (H-PcTs), aluminum (III) phthalocyanine tetrasulfonic acid (Al-PcTs), zinc (II) phthalocyanine tetrasulfonic acid (Zn-PcTs), nickel (II) phthalocyanine tetrasulfonic acid (Ni-PcTs), and copper phthalocyanine tetrasulfonic acid (Cu-PcTs). These phthalocyanine tetrasulfonic acid molecules all include mixtures of different sulfonic acid regioisomers. All of these phthalocyanine tetrasulfonic acid molecules (25 µM) potentiated the activity of ciprofloxacin (40 nM) at similar levels, decreasing CFUs by ~100-fold after 24 hours (FIG. 1(*d*)).

This result showed that ciprofloxacin potentiating activities of phthalocyanine tetrasulfonic acid molecules that contain a mixture of sulfonic acid regioisomers were not influenced by the identity of the chelated metal ion (FIG. 1 (d)).

Example 6

Broad Spectrum Effectiveness of Potentiating Activity

To confirm that the activity of 4,4-Fe-PcTs was not specific to the gram-negative ATCC25922 *E. coli*, the ability of 4,4-Fe-PcTs to potentiate the activity of ciprofloxacin in another gram-negative (*Pseudomonas aeruginosa* ATCC27853) strain and two gram-positive (*Staphylococcus aureus* ATCC29213 and *Enterococcus faecalis* ATCC29212) strains was evaluated.

Figure 4:
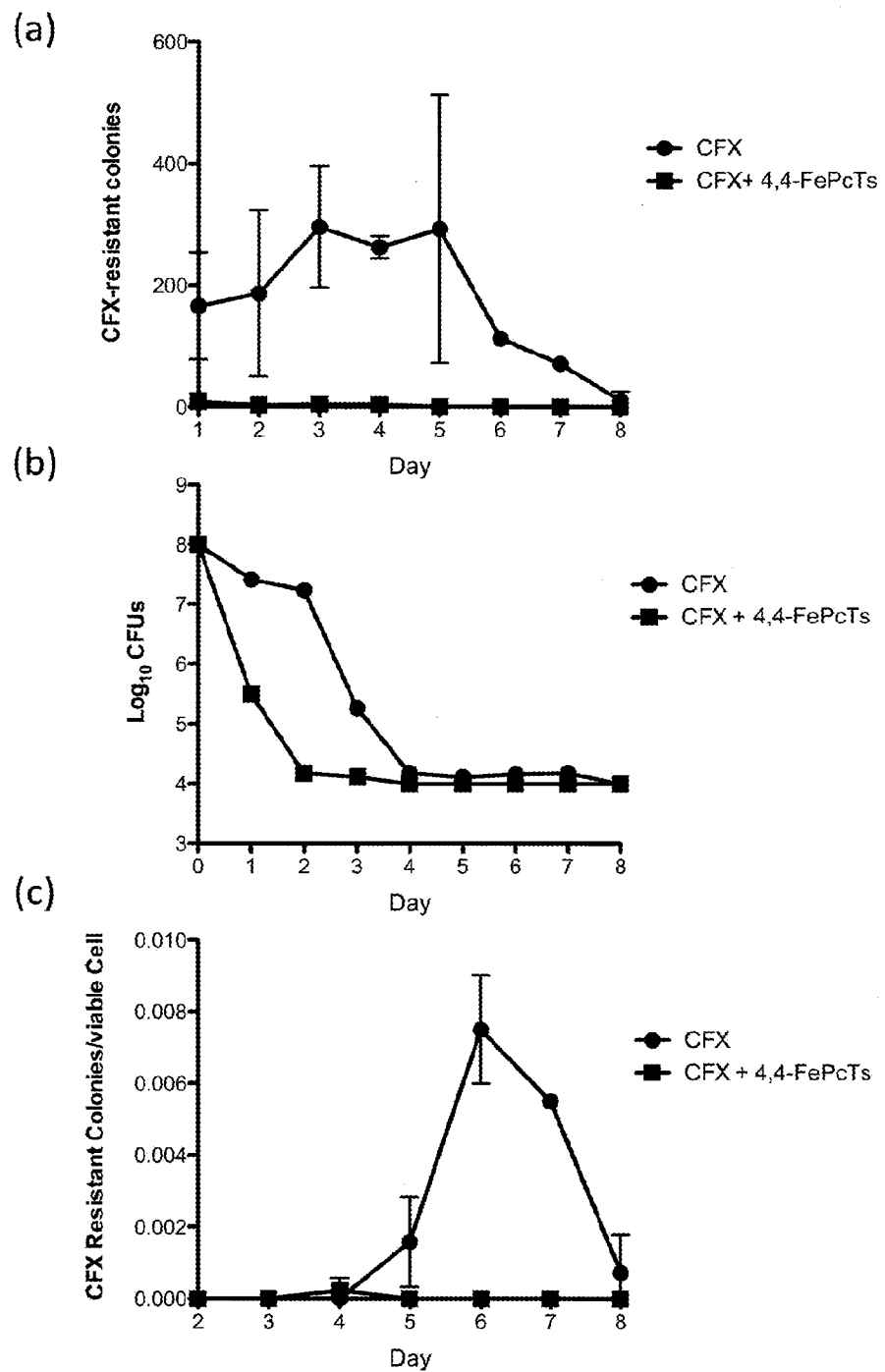
FIGS. 4(a)-4(e) show results demonstrating that 4,4-Fe-PcTs potentiates the activity of ciprofloxacin and reduces ciprofloxacin resistance. ATCC29522 cells ($3\times10^8$) were cultured on LB plates containing ciprofloxacin (CFX) (40 nM) with or without 4,4-Fe-PcTs (25 µM).

As shown in FIG. 2(a), 4,4-Fe-PcTs (at 25 µM) potentiated the activity of ciprofloxacin (at 6.5 µM) in both gram-negative and gram-positive bacteria strains. ATCC27853 was less sensitive to ciprofloxacin than the two gram-positive strains.

Example 7

Potentiation of Bactericidal Versus Bacteriostatic Antibiotics

The ability of 4,4-Fe-PcTs to potentiate the activity of both bactericidal and bacteriostatic antibiotics was assayed. ATCC25922 was co-treated with 4,4-Fe-PcTs and bactericidal antibiotics ciprofloxacin (CFX), ampicillin (AMP), and kanamycin (KAN), which are members of the quinolone, β-lactam, and aminoglycoside families, respectively, and cell viability was monitored. 4,4-Fe-PcTs potentiated the activity of ciprofloxacin, kanamycin, and ampicillin, eliminating all CFUs after 24 hours (FIG. 2(b)).

ATCC25922 was also co-treated with 4,4-Fe- and the bacteriostatic antibiotics chloramphenicol (CAM), tetracycline (TET), and spectinomycin (SPECT). 4,4-Fe-PcTs had a very slight effect on the activity of these bacteriostatic antibiotics. (FIG. 2(b)).

Example 8

Demonstration that 4,4-Fe-PcTs Reduces SOS Induction

To confirm that the bactericidal antibiotic potentiating activity of 4,4-Fe-PcTs was correlated with reduced SOS induction, SOS induction in the *E. coli* strain SS996 was monitored. This strain contains a green fluorescent protein (GFP) regulated by the sulA SOS promoter [17].

SS996 cultures were grown to an optical density at 600 nm ($OD_{600}$) of 0.3. For cultures treated with 4,4-Fe-PcTs, the 4,4-Fe-PcTs was added to give a concentration of 25 µM and the culture was incubated for three hours at 37° C. Antibiotics were then added to yield concentrations of 2.5 µM (CFX), 40 µM (AMP), 43 µM (KAN), 21 µM (TET), 46 µM (CAM), or 808 µM (SPECT). Samples (~$10^6$ cells) were taken immediately before the addition of antibiotics (time zero) and every hour for three hours. Samples were washed once in PBS, and resuspended in PBS prior to analysis by flow cytometry. GFP expression was monitored using flow cytometer (Beckman Coulter, Inc.) with a 488 nm argon laser and a 515-545 nm emission. Flow cytometry data were analyzed using Flowjo (Tree Star, Inc.). The results obtained three hours after addition of antibiotic and/or 4,4-FePcTs are shown in FIGS. 2(c) and 2(d).

4,4-Fe-PcTs reduced the ability of the bactericidal antibiotics ciprofloxacin (CFX) and ampicillin (AMP) to induce the SOS response (FIG. 2(c), in which the curve illustrating results for the sample treated with antibiotic only is shifted to the right as compared with the no treatment, 4,4-Fe-PcTs, and 4,4-Fe-PcTs plus antibiotic treatment groups). Kanamycin (KAN) treatment did not induce the SOS-GFP reporter (FIG. 2(c), in which the curve illustrating results for the sample treated with antibiotic only essentially overlaps with the no treatment, 4,4-Fe-PcTs, and 4,4-Fe-PcTs plus antibiotic treatment groups). Similar results have been reported previously and, without being bound by theory, are attributed to the inhibition of translation by kanamycin [9], which would block GFP expression.

The bacteriostatic antibiotics chloramphenicol (CAM), tetracycline (TET), and spectinomycin (SPECT) induced only very low levels of GFP expression (FIG. 2(d)), indicating that these antibiotics only induce a very low level of SOS response.

Example 9

SOS Response is Inhibited by a Mechanism Independent of Blocking Hydroxyl Radical Production Kohanski et al. showed that bactericidal antibiotics can increase hydroxyl radical formation [9], which causes damage to proteins, lipids, and DNA [20] and induces the SOS response [9]. In contrast, bacteriostatic antibiotics do not induce hydroxyl radical production or the SOS response [9]. To confirm that 4,4-Fe-PcTs inhibited the SOS response by a mechanism independent of blocking hydroxyl radical production, the ability of 4,4-Fe-PcTs to decrease hydroxyl radical levels in the presence of bactericidal antibiotics was assayed. Hydroxyphenyl fluorescein was used to measure hydroxyl radical formation in bacteria [9].

Hydroxyl radical production was measured using flow cytometry with 30-(p-hydroxyphenyl) fluorescein (HPF, Invitrogen) as described previously [9]. ATCC25922 cells were grown to $OD_{600}$ of 0.3. For cultures treated with 4,4-Fe-PcTs, the 4,4-Fe-PcTs was added to give a concentration of 25 µM and the culture was incubated for three hours at 37° C. Ciprofloxacin was then added to give a concentration of 40 nM with HPF (5 mM). Samples (~$10^6$ cells) were taken immediately before the addition of antibiotics (time zero) and every hour for three hours. The samples were washed once in PBS, and resuspended in PBS prior to analysis by flow cytometry. Hydroxyl radical production was monitored using a flow cytometer (Beckman Coulter, Inc.) with a 488 nm argon laser and a 515-545 nm emission. Flow cytometry data were analyzed using Flowjo (Tree Star, Inc.).

4,4-Fe-PcTs did not alter the ability of the bactericidal antibiotic ciprofloxacin to induce hydroxyl radicals. FIG. 2(e) shows the results after three hours of treatment with ciprofloxacin and/or 4,4-Fe-PcTs. In FIG. 2(e), the curve showing data for the 4,4-Fe-PcTs plus ciprofloxacin (CFX) sample is very similar to the curve showing data for the ciprofloxacin (CFX) alone sample, and both curves from the ciprofloxacin-treated samples are shifted slightly to the right of the curve for the no treatment group sample and the curve for the 4,4-Fe-PcTs alone sample. These results are consistent with the ability of 4,4-Fe-PcTs to potentiate the activity of bactericidal antibiotics by inhibiting RecA and blocking induction of the SOS response.

Example 10

Evaluation of Filamentation and Biofilm Formation

To confirm that 4,4-Fe-PcTs interfered with bactericidal antibiotic induction of the SOS response, the ability of 4,4-Fe-PcTs to reduce the ability of ciprofloxacin to induce in vitro filamentation and biofilm formation was assessed. Filamentation and biofilm formation are two biological processes that are mediated by the SOS response [21,22]. Induction of the SOS response leads to increased levels of SulA, a cell division inhibitor [23], and bacterial filamentation. SOS regulators, RecA and LexA, have been shown to be involved in regulating biofilm formation caused by DNA damaging agents [22].

Filamentation Assay:

Overnight cultures of *E. coli* ATCC25922 were grown in LB at 37° C. Cells were then diluted to $10^6$ cells/ml and treated with ciprofloxacin (CFX) (40 nM) or 4,4-Fe-PcTs (25 µM) or ciprofloxacin (CFX) (40 nM)+4,4-Fe-PcTs (25 µM) for three hours. The cells were stained using the standard Gram staining technique and imaged using light microscopy at 100× magnification.

Biofilm Formation Assay:

Biofilm formation on a plastic surface was analyzed using a 96-well plate (Falcon) as described previously [21]. ATCC29522 cells were diluted in LB broth to $1\times10^5$ CFUs/ml. A 100 µl aliquot of cells was added to each well in the plate. Ciprofloxacin (CFX) was then added at a final concentration of 40 nM to each well and plates were incubated at 37° C. for 20 hours. Wells were aspirated and washed three times with 150 µl of PBS. Wells were stained with 120 µl of 0.1% crystal violet (Fisher) for 20 minutes. The crystal violet stain was aspirated and wells were washed three times with 150 µl of PBS. The plate was air-dried and the dye bound to adherent cells was resolubilized with 150 µl of 30% (v/v) glacial acetic acid (Fisher). The plate was incubated at room temperature for 20 minutes with shaking. The biofilm formation was quantified by measuring the $OD_{600\ nm}$ using a plate reader.

Figure 2:
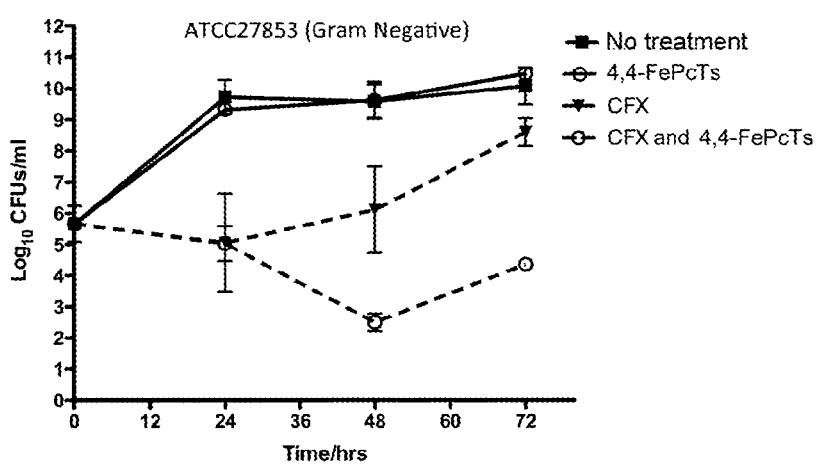
FIG. 2(a) shows 4,4-Fe-PcTs activity in gram-negative and gram-positive bacteria. (i) Potentiation of ciprofloxacin activity by 4,4-Fe-PcTs in P. aeruginosa ATCC27853 (gram-negative). Cells were untreated (No treatment), treated with 4,4-Fe-PcTs (25 µM), treated with ciprofloxacin (CFX) (6.5 µM), or treated with ciprofloxacin (CFX) (6.5 µM) and 4,4-Fe-PcTs (25 µM). CFUs/ml were determined at indicated time points. (ii) Potentiation of ciprofloxacin activity by 4,4-Fe-PcTs in E. faecalis ATCC29213 (gram-positive). Treatments were the same as in (i). (iii) Potentiation of ciprofloxacin activity by 4,4-Fe-PcTs in S. aureus ATCC29212 (gram positive). Treatments were the same as in (i). Error bars represent the standard deviation from three independent experiments.
FIG. 2(b) shows 4,4-Fe-PcTs activity with bactericidal and bacteriostatic antibiotics. Survival of E. coli ATCC25922 cells treated with 4,4-Fe-PcTs (25 µM) and the following bactericidal antibiotics is shown: (i) ciprofloxacin (CFX) (40 nM), (ii) kanamycin (KAN) (43 µM), and (iii) ampicillin (AMP) (40 µM) or bacteriostatic antibiotics, (iv) chloramphenicol (CAM) (46 µM), (v) tetracycline (TET) (21 µM), and (vi) spectinomycin (SPECT) (808 µM). Cells were untreated (No treatment), treated with 4,4-Fe-PcTs (25 µM), treated with the indicated antibiotic, or treated with 4,4-Fe-PcTs (25 µM) and the indicated antibiotic. CFUs/ml were determined at indicated time points. Errors bars represent the standard deviation from three independent experiments.
FIG. 2(c) shows the SOS response induction in E. coli treated with 4,4-Fe-PcTs and bactericidal antibiotics. SOS response was monitored using an E. coli strain (SS996) engineered to express GFP under the control of the LexA-regulated sulA promoter. GFP expression was measured using flow cytometry three hours after addition of CFX (2.5 µM), AMP (40 µM), or KAN (43 µM) in the presence or absence of 4,4-Fe-PcTs (25 µM).
FIG. 2(d) shows SOS response induction in E. coli treated with 4,4-Fe-PcTs and bacteriostatic antibiotics. GFP expression was measured using flow cytometry three hours after addition of TET (21 µM), CAM (46 µM), or SPECT (808 µM) in the presence or absence of Fe-PcTs (25 µM).
FIG. 2(e) shows hydroxyl radical production in E. coli by ciprofloxacin (CFX) and 4,4-Fe-PcTs. ATCC25922 cells were treated with ciprofloxacin (40 nM) and/or 4,4-Fe-PcTs (25 µM) for three hours. Cells were then treated with hydroxyphenyl fluorescein (HPF) and hydroxyl radical levels measured by flow cytometry.
FIG. 2(f) shows inhibition of ciprofloxacin-induced E. coli filamentation by 4,4-Fe-PcTs. ATCC25922 cells were treated with ciprofloxacin (CFX) (40 nM) and/or 4,4-Fe-PcTs (25 µM) for three hours. Cells were then imaged at 100× magnification after Gram staining.
FIG. 2(g) shows inhibition of ciprofloxacin-induced biofilm formation on a plastic surface by 4,4-Fe-PcTs. Cell mass of biofilms forming on the wall of the 96-well plate after 24 hour static incubation with ciprofloxacin (40 nM) and/or Fe-PcTs (25 µM) was determined spectrophotometrically by measuring the optical density at 600 nm after crystal violet staining. Error bars represent the standard deviation from three-independent experiments. * represents P-values <0.05 and ** represents P <0.01.
Figure 2:
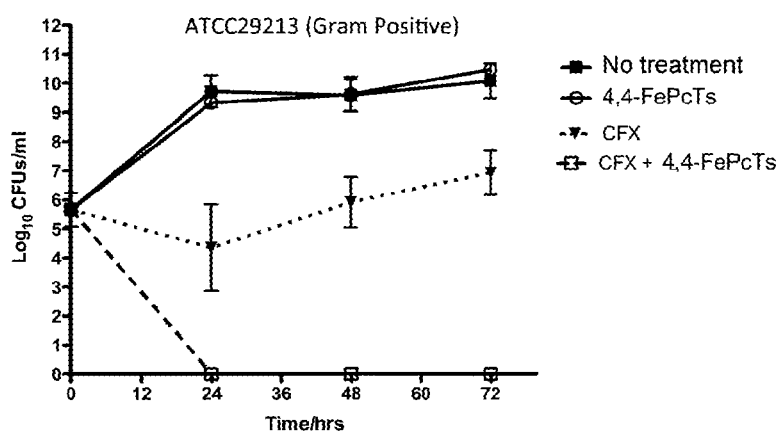
Figure 2:
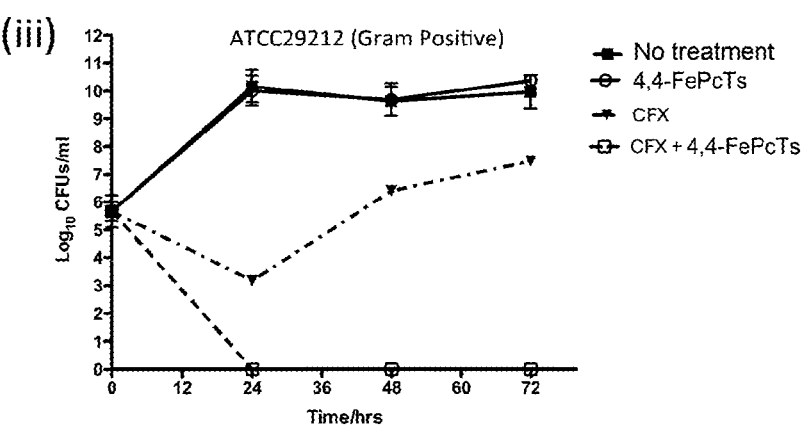

Consistent with the ability of 4,4-Fe-PcTs to block ciprofloxacin-induced SOS response, 4,4-Fe-PcTs reduced the ability of ciprofloxacin to induce in vitro filamentation (FIG. 2(*f*)) and biofilm formation (FIG. 2(*g*)).

Example 11

Evaluation of Mechanism of Inhibition of RecA

In principle, RecA can be inhibited by targeting three functionally important processes: recruitment and polymerization, ATP binding, and DNA binding. These processes are connected by allosteric regulatory mechanisms and are difficult to differentiate biochemically from each other. To confirm that 4,4-Fe-PcTs and 3,4-Cu-PcTs do not solely inhibit RecA ATPase activity, the ability of these phthalocyanine tetrasulfonic acid molecules to inhibit RecA DNA-binding (both double stranded and single stranded DNA), DNA strand-exchange, and LexA cleavage activities was measured as described below.

Double-Stranded DNA-Binding Assay:

EcRecA (4 µM), a 1.0-kb double-stranded DNA (dsDNA) PCR product (12 µM in base pairs), and indicated concentrations of 4,4-Fe-PcTs or 3,4-Cu-PcTs were incubated in binding buffer (5 mM $MgAc_2$, 50 mM Tris-Hepes at pH 7.6) for 10 minutes at 37° C. EcRecA bound (slower migrating) and unbound dsDNA were resolved using a 1.0% agarose gel. The gel was stained with ethidium bromide and the fluorescence emission in the gel was recorded using a Kodak GelLogic 200 system.

Single-Stranded Oligonucleotide-Binding Assay:

EcRecA (15 µM), fluorescein-labeled oligonucleotide (1 µM) (FAM43: 5'-Fluorescein-TTTTG CGGAT GGCTT AGAGC TTAAT TGCTG AATCT GGTGC TGT-3' (SEQ ID NO:1), and indicated amounts of 4,4-Fe-PcTs or 3,4-Cu-PcTs were incubated in binding buffer (5 mM $MgAc_2$, 50 mM Tris-Hepes at pH 7.6) for 10 minutes at 37° C. EcRecA bound and unbound FAM43 were resolved using a 2.0% agarose gel. The fluorescence emission in the gel was recorded using a Kodak GelLogic 200 system.

Strand Exchange Assay Using Synthetic Oligonucleotides:

Three oligonucleotides (FAM43; 45A: 5'-ACAGC ACCAG ATTCA GCAAT TAAGC TCTAA GCCAT G-3' (SEQ ID NO:2); 55A: 5'-GATGG CTTAG AGCTT AATTG CTGAA TCTGG T GCTG T-3' (SEQ ID NO:3)) were obtained from Integrated DNA Technologies. EcRecA (5 µM) was incubated with indicated concentrations of 4,4-Fe-PcTs or 3,4-Cu-PcTs in strand exchange buffer (2 mM ATP-γ-S(Sigma-Aldrich), 10 mM $MgAc_2$, 100 mM KAc, 50 mM Hepes-Tris buffer at pH 7.6, 0.1% v/v 2-mercaptoethanol) for 10 minutes at 37° C. FAM43 (0.35 µM) was added and the reaction was incubated for 2 minutes. The reaction was started by the addition of 0.35 µM of the dsDNA substrate (annealing product of equimolar oligonucleotides 45A and 55A). The reaction was stopped at 30 minutes by adding EDTA to a final concentration of 20 mM and trypsin to a final concentration of 1 µg/µl. After 10 minutes, 10 µl of the reaction was mixed with 5 µl of loading buffer (30% glycerol and 0.1% bromophenol blue) and products were resolved using a 20% native acrylamide gel. The fluorescence emission in the gel was recorded using a Kodak GelLogic 200 system.

LexA Cleavage Assay:

The LexA cleavage reaction (10 µl) contained 1 µM poly-$(dT)_{45}$, 2 µM EcRecA, 10 µM EcLexA, 0.1 mM ATP-γ-S, 20 mM $MgAc_2$, 50 mM Hepes-Tris at pH 7.6 and indicated concentrations of 4,4-Fe-PcTs or 3,4-Cu-PcTs. The reaction was incubated for 120 minutes at 21° C. and stopped by the addition of 5 µl of loading buffer (30% glycerol, 10% SDS, 0.2 M Tris-HCl at pH 6.8, 0.1% v/v 2-mercaptoethanol and 0.1% w/v bromophenol blue). The products were resolved using a 13% SDS-polyacrylamide gel. The proteins were stained with Coomassie Blue-R250.

Figure 3:
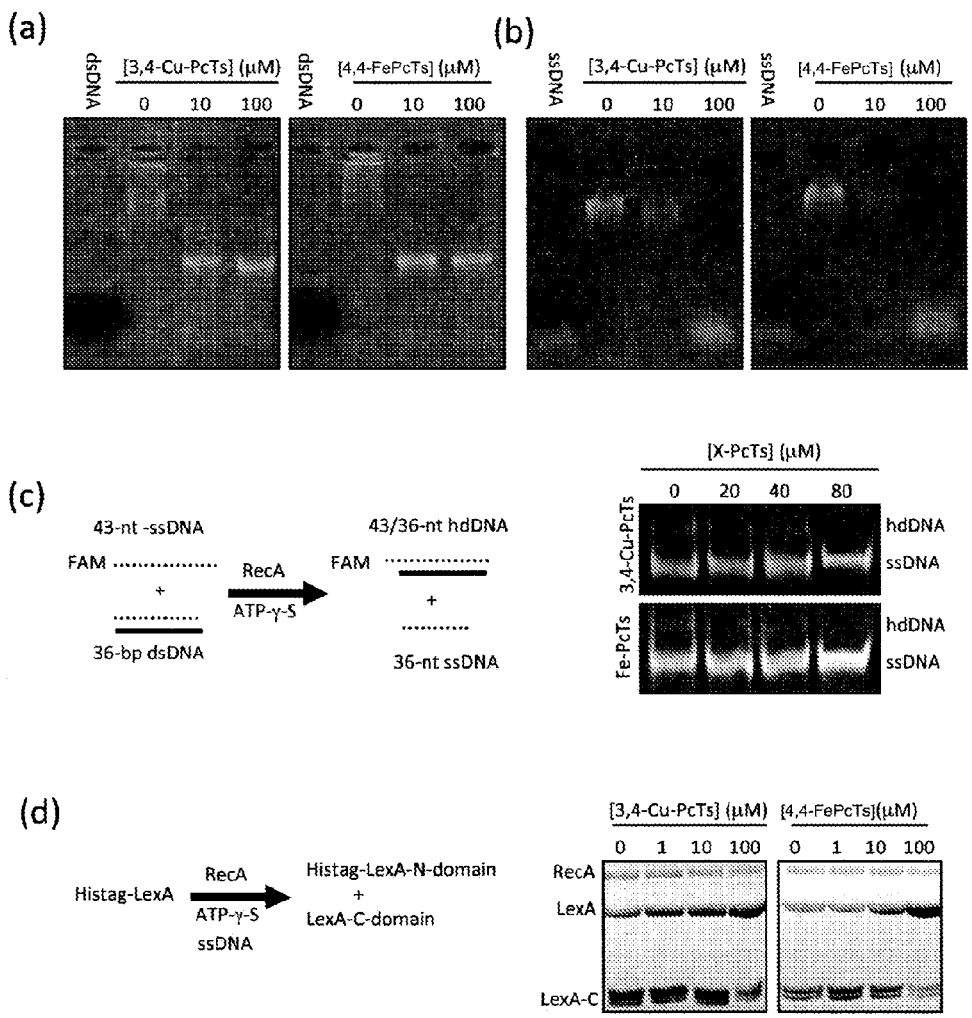
FIGS. 3(a)-3(f) show inhibition of RecA activities by 4,4-Fe-PcTs and 3,4-Cu-PcTs.

The results show that 4,4-Fe-PcTs and 3,4-Cu-PcTs inhibited double-stranded DNA (dsDNA)-binding (FIG. 3(*a*), where shorter bands (faster migrating) are visible at 10 µM and 100 µM concentrations but not at 0 µM concentration) and single-stranded DNA (ssDNA)-binding (FIG. 3(*b*), where a large band (slower migrating) is visible at 0 µM concentrations, partially visible at 10 µM concentrations, and not visible at 100 µM concentrations) activity in the micromolar range (i.e. higher concentrations of phthalocyanine tetrasulfonic acid molecules reduced the amount of the slower migrating RecA-DNA complex), with 4,4-Fe-PcTs showing slightly higher activity.

4,4-Fe-PcTs and 3,4-Cu-PcTs also inhibited DNA strand-exchange (FIG. 3(*c*)) (i.e. higher concentrations of phthalocyanine tetrasulfonic acid compounds decrease the amount of slower migrating heteroduplex DNA) and LexA cleavage (FIG. 3(*d*) (at higher concentrations of phthalocyanine tetrasulfonic acid compounds, less of the LexA (25 KD) is cleaved to yield the faster migrating cleaved LexA products (LexA-C, Histag-EcLexA-N-domain, 9 KD plus EcLexA-C-domain, 16 KD)).

Both DNA strand-exchange and LexA cleavage assays were carried out in the presence of ATPγS, an analogue known to stabilize the RecA-DNA complex better than ATP [24]. In agreement with this, it was observed that higher concentrations (80 μM to 100 μM) of 4,4-Fe-PcTs or 3,4-Cu-PcTs were needed to inhibit DNA strand-exchange and LexA-cleavage activities of RecA compared to RecA dsDNA and ssDNA binding activities. These observations suggest that 4,4-Fe-PcTs and 3,4-Cu-PcTs compete with DNA binding in a manner similar to the metatungstate RecA inhibitor [15].

Example 12

Inhibition of RecA Filament Formation

To determine whether 3,4-Cu-PcTs inhibited RecA filament formation, size exclusion chromatography and electron microscopy were used to assay RecA polymerization in the presence and absence of 3,4-Cu-PcTs.

Size Exclusion Assay:

RecA (5 μM) and 3,4-Cu-PcTs (50 μM) were incubated in 0.15 M NaCl and 0.05 M Tris-HCl buffer at pH 7.4. The protein complexes were resolved by loading 2 ml of RecA/3,4-Cu-PcTs on a Pharmacia sephacryl S-300 column pre-equilibrated with the running buffer. The size exclusion column was calibrated with standard proteins with molecular weights of 35, 67, and 167 KD. Elution of proteins off the size exclusion column was monitored using absorbance at 280 nm.

Electron Microscope to Assess RecA Filament Formation:

RecA protein was prepared as described [25]. RecA-ds-DNA-AMPPNP complexes formed by incubating RecA (3.5 μM), calf thymus dsDNA (Sigma) at a 40 dsDNA:1 RecA ratio (w/w), AMP-PNP (adenosine 5'-(β,γ-imido)triphosphate) (Sigma) (1.3 mM), MgAc$_2$ (Sigma) (2 mM), triethanolamine-HCl (Fisher) buffer (25 mM, pH 7.2) with or without 3,4-Cu-PcTs (3.75 μM) at 37° C. for 10 minutes. Samples were applied to carbon-coated grids and stained with 2% uranyl acetate (w/v). Images were recorded on film with a Tecnai 12 electron microscope operating at 80 keV with a nominal magnification of 30,000×. Negatives were scanned with a Nikon Coolscan 8000 densitometer at a raster of 4.2 Å/pixel.

Addition of 3,4-Cu-PcTs reduced the molecular weight of the RecA complex to a size consistent to the RecA ring-shaped hexamer storage complex (FIG. 3, panel (e)). 3,4-Cu-PcTs also inhibited ssDNA-stimulated RecA filament formation as shown by electron microscopy (FIG. 3, panel (f).

Example 13

In Vitro Use of Phthalocyanine Tetrasulfonic Acid Compounds to Inhibit Development of Antibiotic Resistance An in vitro mutagenesis assay [1] was used to measure the ability of 4,4-Fe-PcTs to block the acquisition of ciprofloxacin-induced resistance in ATCC25922 E. coli. ATCC25922 cells were plated on media containing ciprofloxacin in the presence or absence of 4,4-Fe-PcTs and cultured for 10 days. Colonies that appeared early in the assay (days 1 and 2) are believed to arise from pre-existing ciprofloxacin resistance mutations [1]. Colonies that appear later in the incubation (days 3 to 8) are due to ciprofloxacin resistance mutations acquired during exposure to ciprofloxacin or pre-existing mutations with a slow growth phenotype [1].

To distinguish between these two types of mutants, a reconstruction assay that tests for the time it takes for colonies to appear in the presence of ciprofloxacin was used. Colonies that appear at least two days faster than they appeared in the original ciprofloxacin mutagenesis screen were classified as colonies that acquire resistance after exposure to ciprofloxacin [1]. Colonies that appeared in the same number of days as in the ciprofloxacin resistance assay were classified as colonies with pre-existing mutations [1].

Ciprofloxacin Resistance Assay:

Twenty-five independent colonies of ATCC2592 were used to inoculate 25 LB broth cultures that were incubated at 37° C. for 25 hours. Viable cell counts in these cultures were determined by plating serial dilutions onto LB agar plates. One hundred microliters from each culture (~$10^8$ cells) were plated in duplicate on LB agar containing ciprofloxacin (CFX) (40 nM) or ciprofloxacin (40 nM) and 4,4-Fe-PcTs (25 μM) (CFX+4,4-Fe-PcTs). Three additional 100 μL aliquots from three cultures were also plated on the same media to determine the number of viable cells per day. At 24 hour intervals, visible colonies were counted, removed from the plate, and stored at −80° C. for later use in the reconstruction assay and sequencing. Every 24 hours, in parallel with the resistance assay, small plugs of agar between visible colonies were excised from resistance assay plates. Agar plugs were homogenized in M9 buffer. Dilutions were plated in duplicate on LB plates to determine the total number of viable cells per day. The cells were also plated on LB containing CFX (40 nM) to determine if any CFX-resistant colonies remained after excision [1].

Reconstruction Assay:

Reconstruction assays were used to determine whether ciprofloxacin resistant colonies were due to post-exposure mutation or due to mutation prior to ciprofloxacin exposure. Ciprofloxacin resistant clones isolated from the resistance assay were grown to saturation in LB media in 96 well plates. Cultures were then replica-plated in duplicate using a 96-pin replicator on LB plates to confirm viability and LB plates containing ciprofloxacin (40 nM) to confirm ciprofloxacin resistance. Ciprofloxacin-resistant clones that were isolated in the presence 4,4-Fe-PcTs were replica plated on LB and LB containing 4,4-Fe-PcTs (25 μM) and ciprofloxacin (40 nM). Clones that were resistant before ciprofloxacin exposure were defined as clones that formed colonies on the ciprofloxacin-containing media in the same number of days in the reconstruction assay as in the original resistance assay. Clones that mutated after exposure to ciprofloxacin were defined as clones that formed colonies earlier than in the original resistance assay [1].

Calculation of Ciprofloxacin Resistance Rate:

The rate of ciprofloxacin resistance was defined as the number of ciprofloxacin-resistant mutants per viable cell that evolve as a function of time. The mutation rate represents only those mutations that allow cells to survive and confer resistance to ciprofloxacin. Mutations observed after exposure to ciprofloxacin (post-exposure rate) showed the expected Poisson distribution [26] and the associated rate was determined as the ratio of colonies on a particular day to the number of cells present at the time the cells became resistant, which was approximated as the viable cell count two days prior.

GyrA and ParC Sequencing:

Colonies from the reconstruction assays were streaked on LB agar containing CFX (40 nM). A single colony from each plate was used as a colony PCR template for gyrA and parC gene fragment amplification. A DNA amplicon of 648 bp from nucleotides 24 to 671 of the gyrA gene was amplified using primers and PCR conditions described previously [27].

A DNA amplicon of 395 bp from nucleotides 115 to 509 of the parC gene was amplified using primers and PCR conditions described previously [28]. The PCR products were purified using the Biobasic PCR Purification kit (VWR) and sequenced with PCR primers.

Using these in vitro mutagenesis and reconstruction assays, it was calculated that 29% and 60% of the ciprofloxacin-resistant ATCC25922 colonies isolated were caused by pre-existing mutations in the ciprofloxacin-alone and ciprofloxacin and 4,4-Fe-PcTs assays, respectively (Table 1). These results are consistent with the ability of 4,4-Fe-PcTs to reduce the number of acquired resistance mutations in response to ciprofloxacin exposure. Sequencing analysis of the quinolone resistance-determining region of gyrA and parC genes revealed an aspartate to asparagine mutation at position 87 of gyrA in all ciprofloxacin-resistant clones from both ciprofloxacin and ciprofloxacin and 4,4-Fe-PcTs treated cells. This is a frequent quinolone resistant mutation observed in GyrA [29].

The results show that treatment with both 4,4-Fe-PcTs and ciprofloxacin together reduced the total number of viable and ciprofloxacin-resistant ATCC25922 cells relative to ciprofloxacin treatment alone (FIGS. 4(a) and 4(b)). Since 4,4-Fe-PcTs potentiated the activity of ciprofloxacin, there were fewer cells present that could acquire resistance mutations. To account for the decreased viability in cells treated with 4,4-Fe-PcTs and ciprofloxacin, the ciprofloxacin mutation rate was defined as ciprofloxacin resistant colonies per viable cell per day (FIG. 4(c)) as described previously [1]. For ATCC25922 cells treated with Fe-PcTs and ciprofloxacin, no ciprofloxacin resistant mutants were observed after day 4. In contrast, ATCC25922 cells treated with only ciprofloxacin showed a spike in ciprofloxacin-resistant cells at day 5. These results highlight the ability of 4,4-Fe-PcTs to inhibit the acquisition of ciprofloxacin resistance mutations in an in vitro assay.

Example 14

In Vivo Use of Phthalocyanine Tetrasulfonic Acid Compounds to Inhibit Development of Antibiotic Resistance To establish whether 4,4-Fe-PcTs can inhibit the acquisition of ciprofloxacin resistance in vivo, the activity of 4,4-Fe-PcTs was assayed in a neutrapenic murine bacterial thigh infection model [1,30].

Six-eight week-old, specific-pathogen-free, female CD-1 mice (weight, 25-35 g) were rendered neutropenic by intraperitoneal injection with 150 mg/kg cylcophosphamide (Sigma) four days before infection and 100 mg/kg cyclophosphamide 24 hours before infection. LB broth cultures inoculated from fresh ATCC25922 colonies and cells were grown to the log phase ($OD_{600}$ of approximately 0.3) and diluted 1:1000 in LB broth. Thigh infections were produced by injecting 50 μl (approximately $10^6$ CFUs) of diluted cultures into halothane-anesthetized mice. One group of mice was administrated inteperitoneal injection of 4,4-Fe-PcTs in conjunction with the second dose of cyclophosphamide (24 hours prior infection) (4,4-Fe-PcTs (pre)+CFX). Starting two hours after infection (defined as time zero), mice were administered subcutaneous injections of either 1 mg/kg ciprofloxacin alone (CFX) or co-treatment of 1 mg/kg ciprofloxacin with interperitoneal injection of 10 mg/kg 4,4-Fe-PcTs (4,4-Fe-PcTs+CFX and 4,4-Fe-PcTs (pre)+CFX) every 24 hours for 3 days. After 48 and 72 hours, three mice from each group were sacrificed, and their thighs removed and homogenized to determine the number of viable bacterial cells for both ciprofloxacin-sensitive and ciprofloxacin-resistant ATCC25922 cells. Serial dilutions of homogenates of the infected thigh were plated on LB agar (CFX Sensitive) and LB agar plates containing ciprofloxacin (40 nM) (CFX Resistant) to count viable cells for each of the three treatment groups.

Approximately 50,000 ciprofloxacin-resistant cells were observed after 72 hours of infection when the mice were treated only with ciprofloxacin. Remarkably, no ciprofloxacin resistant cells were observed when mice were co-treated with both ciprofloxacin and 4,4-Fe-PcTs (FIG. 4(d), both the 4,4-Fe-PcTs+CFX and 4,4-Fe-PcTs (pre)+CFX treatment groups). Pretreatment of mice with 4,4-Fe-PcTs prior to infection potentiated the activity of ciprofloxacin more than when mice were only co-treated with ciprofloxacin and 4,4-Fe-PcTs shortly after infection (FIG. 4(d)). No ciprofloxacin-resistant colonies were observed in any mice treated with 4,4-Fe-PcTs, which may reflect the time required for *E. coli* to develop resistance.

Example 15

Assessment of Toxicity 4,4-Fe-PcTs treatment was not toxic to mouse bone marrow at the maximum concentration tested (100 μM) (FIG. 4, panel (e)). The lack of Fe-PcTs toxicity is consistent with other studies showing that PcTs-based molecules are well tolerated by rodents receiving long-term dosing regimens [31]. Further, PcTs-based molecules have been used to block scrapie infection in mouse models [32].

The addition of Fe-PcTs to antibiotic therapies can be applied to a range of bactericidal antibiotics, which will potentiate their activity and prolong their lifespan by reducing the acquisition of antibiotic resistance mutations. In contrast to existing antibiotic combinations aimed at blocking resistance such as Augmentin, which consists of a β-lactam and a β-lactamase inhibitor, Fe-PcTs can be combined with a wide-range of bactericidal antibiotics, providing a general strategy for constructing anti-resistance antibiotic combinations.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole. To the extent that aspects of the exemplary embodiments and examples described above are not mutually exclusive, it is intended that all such combinations and subcombinations are within the scope of the present invention.

REFERENCES

The following references are cited herein, and each such reference is hereby incorporated by reference herein in its entirety:

1. Cirz, R. T., et al., *Inhibition of mutation and combating the evolution of antibiotic resistance*. PLoS Biol, 2005. 3(6): p. e176.
2. Riesenfeld, C., et al., *Adaptive mutations produce resistance to ciprofloxacin*. Antimicrob Agents Chemother, 1997. 41(9): p. 2059-60.
3. Smith, P. A. and F. E. Romesberg, *Combating bacteria and drug resistance by inhibiting mechanisms of persistence and adaptation*. Nat Chem Biol, 2007. 3(9): p. 549-56.

4. McKenzie, G. J., et al., *The SOS response regulates adaptive mutation*. Proc Natl Acad Sci USA, 2000. 97(12): p. 6646-51.
5. Janion, C., *Some aspects of the SOS response system—a critical survey*. Acta Biochim Pol, 2001. 48(3): p. 599-610.
6. Sassanfar, M. and J. W. Roberts, *Nature of the SOS-inducing signal in Escherichia coli. The involvement of DNA replication*. J Mol Biol, 1990. 212(1): p. 79-96.
7. Cirz, R. T. and F. E. Romesberg, *Controlling mutation: intervening in evolution as a therapeutic strategy*. Crit Rev Biochem Mol Biol, 2007. 42(5): p. 341-54.
8. Cirz, R. T., N. Gingles, and F. E. Romesberg, *Side effects may include evolution*. Nat Med, 2006 12(8): p. 890-1.
9. Kohanski, M. A., et al., *A common mechanism of cellular death induced by bactericidal antibiotics*. Cell, 2007. 130 (5): p. 797-810.
10. Beaber, J. W., B. Hochhut, and M. K. Waldor, *SOS response promotes horizontal dissemination of antibiotic resistance genes*. Nature, 2004. 427(6969): p. 72-4.
11. Hastings, P. J., S. M. Rosenberg, and A. Slack, *Antibiotic-induced lateral transfer of antibiotic resistance*. Trends Microbiol, 2004. 12(9): p. 401-4.
12. Raymond-Denise, A. and N. Guillen, *Identification of dinR, a DNA damage-inducible regulator gene of Bacillus subtilis*. J Bacteriol, 1991. 173(22): p. 7084-91.
13. Lusetti, S. L. and M. M. Cox, *The bacterial RecA protein and the recombinational DNA repair of stalled replication forks*. Annu Rev Biochem, 2002. 71: p. 71-100.
14. Karlin, S. and L. Brocchieri, *Evolutionary conservation of RecA genes in relation to protein structure and function*. J Bacteriol, 1996. 178(7): p. 1881-94.
15. Li, Y., Y. He, and Y. Luo, *Crystal structure of an archaeal Rad51 homologue in complex with a metatungstate inhibitor*. Biochemistry, 2009. 48(29): p. 6805-10.
16. Kohanski, M., Dwyer, D. J. and Collins, J. J., *How antibiotics kill bacteria: from targets to networks*. Nature Rev. Microb., 2010. 8: p. 423-435.
17. McCool J D, Long E, Petrosino J F, Sandler H A, Rosenberg S M, Sandler S J., *Measurement of SOS expression in individual Escherichia coli K-12 cells using fluorescence microscopy*. Mol Microbiol. 2004, 53(5): p. 1343-57.
18. Itaya, K., and Ui, M., *A new micromethod for the colorimetric determination of inorganic phosphate*. Clin. Chim. Acta, 1996 14: p. 361-366.
19. Drlica K, and Zhao X. *DNA gyrase, topoisomerase IV, and the 4-quinolones*. Microbiol Mol Biol Rev, 1997. 61: p. 377-392.
20. Farr, S. B., and Kogoma, T. *Oxidative stress responses in Escherichia coli and Salmonella typhimurium*. Microbiol. Rev, 1991,. 55: p. 561-585.
21. Gotoh H, Kasaraneni N, Devineni N, Dallo S F, and Weitao T. *SOS involvement in stress-inducible biofilm formation*. Biofouling. 2010, 26(5): p. 603-11.
22. Bi E, Lutkenhaus J. *Cell division inhibitors SulA and MinCD prevent formation of the FtsZ ring*. J Bacteriol. 1993, 175(4): p. 1118-25.
23. Huisman O, D'Ari R, Gottesman S. *Cell-division control in Escherichia coli: specific induction of the SOS function SfiA protein is sufficient to block septation*. Proc Natl Acad Sci USA. 1984, 81(14): p. 4490-4.
24. Kowalczykowski, S. C., et al., *Biochemistry of homologous recombination in Escherichia coli*. Microbiol Rev, 1994. 58(3): p. 401-65.
25. Yu X, Egelman E H., *Direct visualization of dynamics and co-operative conformational changes within RecA filaments that appear to be associated with the hydrolysis of adenosine 5'-O-(3-thiotriphosphate)*. J Mol Biol. 1992, 225(1): p. 193-216.
26. Rosenberg, S. M. *Evolving responsibly: Adaptive mutation*. Nat Rev Genetics. 2010, 2: p. 504-15.
27. Oram, M., and Fisher, L. M., *4-Quinolone resistance mutations in the DNA gyrase of Escherichia coli clinical isolates identified by using the polymerase chain reaction*. Antimicrob Agents Chemother. 1991, 35(2): p. 387-9.
28. Vila, J., Ruiz, J., Goni, P., De Anta, M. T., *Detection of mutations in parC in quinolone resistant clinical isolates of Escherichia coli*. Antimicrob Agents Chemother. 1996, 40(2): p. 491-3.
29. Barnard, F. M., Maxwell, A., *Interaction between DNA gyrase and quinolones: effects of alanine mutations at GyrA subunit residues Ser(83) and Asp(87)*. Antimicrob Agents Chemother, 2001. 45(7): p. 1994-2000.
30. Zuluaga, A. F., et al., *Neutropenia induced in outbred mice by a simplified low-dose cyclophosphamide regimen: characterization and applicability to diverse experimental models of infectious diseases*. BMC Infect Dis, 2006. 6: p. 55.
31. Caughey W S, Priola S A, Kocisko D A, Raymond L D, Ward A, Caughey B., *Cyclic tetrapyrrole sulfonation, metals, and oligomerization in antiprion activity*. Antimicrob Agents Chemother. 2007, 51(11): p. 3887-94.
32. Priola S A, Raines A, Caughey W. J., *Prophylactic and therapeutic effects of phthalocyanine tetrasulfonate in scrapie-infected mice*. Infect Dis. 2003, 188(5): p. 699-705.

What is claimed is:

1. A method of: treating a subject being administered a bactericidal antibiotic to treat a bacterial infection; potentiating the effect of a bactericidal antibiotic in a subject being administered the bactericidal antibiotic to treat a bacterial infection; and/or inhibiting development of resistance to a bactericidal antibiotic in a subject being administered the bactericidal antibiotic to treat a bacterial infection; the method comprising administering a phthalocyanine tetrasulfonic acid compound to the subject.

2. A method as defined in claim 1, wherein:
the bactericidal antibiotic is administered at a daily dose in the range of 0.1 mg/kg to 10 mg/kg; and/or
the phthalocyanine tetrasulfonic acid compound is administered at a daily dose in the range of 1 mg/kg to 20 mg/kg.

3. A method as defined in claim 1, wherein:
the bactericidal antibiotic and the phthalocyanine tetrasulfonic acid compound are administered to the subject separately;
the bactericidal antibiotic and the phthalocyanine tetrasulfonic acid compound are administered to the subject concurrently;
the bactericidal antibiotic is administered by topical application, injection or delivery to a desired location, intravenous injection, or intramuscular injection;
the phthalocyanine tetrasulfonic acid compound is administered by topical application, injection or delivery to a desired location, intravenous injection, or intramuscular injection;
the bactericidal antibiotic is administered by oral, parenteral, cutaneous, rectal, nasal, or vaginal application; and/or
the phthalocyanine tetrasulfonic acid compound is administered by oral, parenteral, cutaneous, rectal, nasal, or vaginal application.

4. A method as defined in claim 1, wherein the subject is a mammal.

5. A composition for potentiating the effect of a bactericidal antibiotic for treating a bacterial infection, and/or for inhibiting the development of resistance to a bactericidal antibiotic for treating a bacterial infection, the composition comprising the bactericidal antibiotic and a phthalocyanine tetrasulfonic acid compound.

6. A composition as defined in claim 5, comprising between 1 and 1000 mg of the antibiotic, and/or between 10 and 2000 mg of the anionic phthalocyanine compound.

7. A composition as defined in claim 5, wherein the bactericidal antibiotic comprises an activator of the SOS response.

8. A composition as defined in claim 7, wherein the antibiotic that comprises an activator of the SOS response is defined as an antibiotic that produces a 10%, 20%, 30%, 40%, 50%, 60%, 70%, 80%, 90%, 100%, five-fold, ten-fold, twenty-fold or one hundred-fold increase in the induction of SOS response in a bacteria treated with the antibiotic, as measured by expression of GFP regulated by the sulA SOS promoter when the bacteria are exposed to the antibiotic.

9. A method of: treating a subject being administered a bacteriostatic antibiotic; potentiating the effect of a bacteriostatic antibiotic in a subject being administered the bacteriostatic antibiotic; and/or inhibiting development of resistance to a bacteriostatic antibiotic in a subject being administered the bacteriostatic antibiotic to treat a bacterial infection; the method comprising administering a phthalocyanine tetrasulfonic acid compound to the subject and, administering the bacteriostatic antibiotic at a dose or concentration sufficient that the bacteriostatic antibiotic activates the SOS response or acts as a bactericidal antibiotic, using the bacteriostatic antibiotic against a species of bacteria against which the bacteriostatic antibiotic activates the SOS response or acts as a bactericidal antibiotic, or administering the bacteriostatic antibiotic together with an agent that causes the bacteriostatic antibiotic to activate the SOS response or act as a bactericidal antibiotic.

10. A composition as defined in claim 5, wherein the antibiotic comprises a β-lactam antibiotic, an aminoglycoside antibiotic, or a quinolone antibiotic.

11. A composition as defined in claim 5, wherein the antibiotic comprises a DNA gyrase inhibitor or a topoisomerase inhibitor.

12. A composition as defined in claim 5, wherein the antibiotic comprises ciprofloxacin, ampicillin, or kanamycin.

13. A composition as defined in claim 5, wherein the anionic phthalocyanine compound has the general formula:

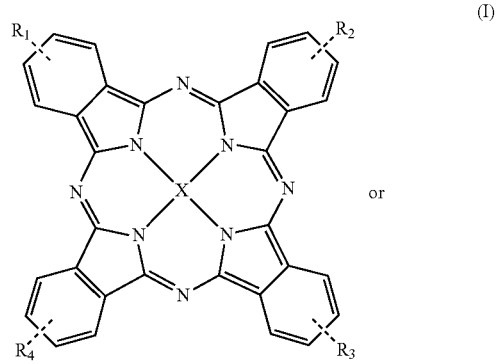

(I) or

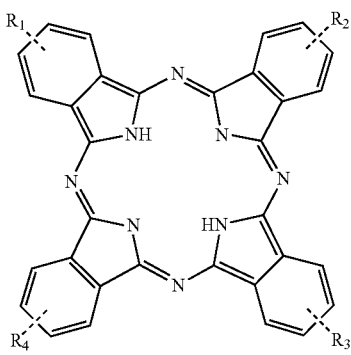

(II)

wherein X comprises any compound or element that can form a coordination complex with phthalocyanine and wherein $R_1$, $R_2$, $R_3$ and $R_4$ are sulfonate groups.

14. A composition as defined in claim 13, wherein X is $FeO_2$, Cu, Al, Zn, or Ni.

15. A composition as defined in claim 5, wherein the anionic phthalocyanine compound comprises iron (III) phthalocyanine-4,4',4'',4'''-tetrasulfonic acid or copper phthalocyanine-3,4',4'',4'''-tetrasulfonic acid.

16. A composition as defined in claim 13, wherein $R_1$, $R_2$, $R_3$ and $R_4$ are —$SO_3^-$.

17. A composition as defined in claim 5, wherein the anionic phthalocyanine compound comprises a 4,4',4'',4'''-phthalocyanine tetrasulfonic acid compound or a 3,4',4'',4'''-phthalocyanine tetrasulfonic acid compound.

18. A composition as defined in claim 5, wherein the anionic phthalocyanine compound is water-soluble.

19. A method according to claim 1 for treating a bacterial infection.

20. A method according to claim 1, wherein the bactericidal antibiotic is used to treat an infection caused at least in part by *Escherichia coli*, *Pseudomonas aeruginosa*, *Staphylococcus aureus*, or *Enterococcus faecalis*.

* * * * *

SEQUENCE LISTING

```
<160> NUMBER OF SEQ ID NOS: 3

<210> SEQ ID NO 1
<211> LENGTH: 43
<212> TYPE: DNA
<213> ORGANISM: artificial sequence
<220> FEATURE:
<223> OTHER INFORMATION: probe

<400> SEQUENCE: 1
ttttgcggat ggcttagagc ttaattgctg aatctggtgc tgt            43

<210> SEQ ID NO 2
<211> LENGTH: 36
<212> TYPE: DNA
<213> ORGANISM: artificial sequence
```

-continued

```
<220> FEATURE:
<223> OTHER INFORMATION: synthetic construct

<400> SEQUENCE: 2
acagcaccag attcagcaat taagctctaa gccatg                                36

<210> SEQ ID NO 3
<211> LENGTH: 36
<212> TYPE: DNA
<213> ORGANISM: artificial sequence
<220> FEATURE:
<223> OTHER INFORMATION: synthetic construct

<400> SEQUENCE: 3
gatggcttag agcttaattg ctgaatctgg tgctgt                                36
```